(12) United States Patent
Pletcher

(10) Patent No.: US 9,708,467 B2
(45) Date of Patent: Jul. 18, 2017

US009708467B2

(54) POLYMER COMPOSITIONS COMPRISING ONE OR MORE PROTECTED ANTIOXIDANTS

(71) Applicant: Zimmer, Inc., Warsaw, IN (US)

(72) Inventor: Dirk Pletcher, Walkerton, IN (US)

(73) Assignee: ZIMMER, INC., Warsaw, IN (US)

( * ) Notice: Subject to any disclaimer, the term of this patent is extended or adjusted under 35 U.S.C. 154(b) by 0 days.

(21) Appl. No.: 15/026,153

(22) PCT Filed: Sep. 30, 2014

(86) PCT No.: PCT/US2014/058241
§ 371 (c)(1),
(2) Date: Mar. 30, 2016

(87) PCT Pub. No.: WO2015/050851
PCT Pub. Date: Apr. 9, 2015

(65) Prior Publication Data
US 2016/0222190 A1    Aug. 4, 2016

Related U.S. Application Data

(60) Provisional application No. 61/885,316, filed on Oct. 1, 2013.

(51) Int. Cl.
| | | |
|---|---|---|
| C08F 2/46 | (2006.01) | |
| C08G 61/04 | (2006.01) | |
| C08K 5/52 | (2006.01) | |
| C08K 5/529 | (2006.01) | |
| A61L 27/16 | (2006.01) | |

(52) U.S. Cl.
CPC ............... *C08K 5/52* (2013.01); *A61L 27/16* (2013.01); *C08K 5/529* (2013.01); *A61L 2430/24* (2013.01)

(58) Field of Classification Search
CPC  C08K 5/52; C08K 5/529; A61L 27/16; A61L 30/24; A61L 2430/24; C08L 23/06
USPC .................................. 522/126, 113, 1; 520/1
See application file for complete search history.

(56) References Cited

U.S. PATENT DOCUMENTS

| | | | |
|---|---|---|---|
| 5,308,549 A | 5/1994 | Laermer et al. | |
| 5,414,049 A | 5/1995 | Sun et al. | |
| 5,559,167 A | 9/1996 | Mahood | |
| 5,577,368 A | 11/1996 | Hamilton et al. | |
| 5,721,334 A | 2/1998 | Burstein et al. | |
| 5,753,182 A | 5/1998 | Higgins | |
| 5,824,411 A | 10/1998 | Shalaby et al. | |
| 5,827,904 A | 10/1998 | Hahn | |
| 5,879,400 A | 3/1999 | Merrill et al. | |
| 6,017,975 A | 1/2000 | Saum et al. | |
| 6,087,553 A | 7/2000 | Cohen et al. | |
| 6,087,559 A | 7/2000 | Nichols | |
| 6,156,845 A | 12/2000 | Saito et al. | |
| 6,156,913 A | 12/2000 | Hyatt | |
| 6,184,265 B1 | 2/2001 | Hamilton et al. | |
| 6,204,257 B1 | 3/2001 | Stella et al. | |
| 6,228,900 B1 | 5/2001 | Shen et al. | |
| 6,231,804 B1 | 5/2001 | Yamauchi et al. | |
| 6,242,227 B1 | 6/2001 | Millis et al. | |
| 6,242,507 B1 | 6/2001 | Saum et al. | |
| 6,245,276 B1 | 6/2001 | McNulty et al. | |
| 6,277,390 B1 | 8/2001 | Schaffner | |
| 6,391,390 B1 | 5/2002 | Boisseau et al. | |
| 6,432,349 B1 | 8/2002 | Pletcher et al. | |
| 6,437,048 B1 | 8/2002 | Saito et al. | |
| 6,448,315 B1 | 9/2002 | Lidgren et al. | |
| 6,464,926 B1 | 10/2002 | Merrill et al. | |
| 6,503,439 B1 | 1/2003 | Burstein | |
| 6,558,794 B1 | 5/2003 | Fehrenbacher et al. | |
| 6,562,540 B2 | 5/2003 | Saum et al. | |
| 6,620,198 B2 | 9/2003 | Burstein et al. | |
| 6,627,141 B2 | 9/2003 | McNulty et al. | |
| 6,641,617 B1 | 11/2003 | Merrill et al. | |
| 6,664,308 B2 | 12/2003 | Sun et al. | |
| 6,664,317 B2 | 12/2003 | King, III | |
| 6,692,679 B1 | 2/2004 | McNulty et al. | |
| 6,786,933 B2 | 9/2004 | Merrill et al. | |
| 6,818,020 B2 | 11/2004 | Sun et al. | |
| 6,818,172 B2 | 11/2004 | King et al. | |
| 6,852,772 B2 | 2/2005 | Muratoglu et al. | |
| 6,853,772 B2 | 2/2005 | Battiato et al. | |
| 6,872,764 B2 | 3/2005 | King, III | |
| 6,933,026 B2 | 8/2005 | Mauze | |
| 7,094,472 B2 | 8/2006 | Du Plessis et al. | |
| 7,160,492 B2 | 1/2007 | King | |
| 7,166,650 B2 | 1/2007 | Muratoglu et al. | |

(Continued)

FOREIGN PATENT DOCUMENTS

| | | |
|---|---|---|
| AU | 2006283596 A1 | 1/2007 |
| AU | 2006350369 A1 | 8/2008 |
| AU | 2008236996 A1 | 10/2008 |
| AU | 2012203503 B2 | 5/2014 |
| CA | 2619937 A1 | 3/2007 |
| CA | 2669386 A1 | 8/2008 |
| CA | 2619502 C | 11/2012 |
| CS | 221403 B1 | 4/1983 |
| CZ | 221405 B1 | 2/1986 |
| EP | 0560279 A1 | 9/1993 |
| EP | 0727195 A2 | 8/1996 |

(Continued)

OTHER PUBLICATIONS

US 7,253,214, 8/2007, McKellop et al. (withdrawn).

(Continued)

*Primary Examiner* — Jessica E Whiteley
(74) *Attorney, Agent, or Firm* — Schwegman Lundberg & Woessner, P.A.

(57) ABSTRACT

Certain embodiments described herein are directed to polymer compositions including a protected antioxidant. In some examples, the compositions can also include a deprotected antioxidant, an unprotected antioxidant or both. Methods of producing compositions including a protected antioxidant and articles including a protected antioxidant are also described.

20 Claims, No Drawings

(56) References Cited

U.S. PATENT DOCUMENTS

| | | |
|---|---|---|
| 7,214,764 B2 | 5/2007 | King |
| 7,259,198 B2 | 8/2007 | Vaillant |
| 7,304,097 B2 | 12/2007 | Muratoglu et al. |
| 7,323,522 B2 | 1/2008 | Ideno et al. |
| 7,335,697 B2 | 2/2008 | King et al. |
| 7,384,430 B2 | 6/2008 | Greer et al. |
| 7,431,874 B2 | 10/2008 | Muratoglu et al. |
| 7,435,372 B2 | 10/2008 | Mimmnaugh et al. |
| 7,445,641 B1 | 11/2008 | Ornberg et al. |
| 7,498,365 B2 | 3/2009 | Muratoglu et al. |
| 7,507,774 B2 | 3/2009 | Muratoglu et al. |
| 7,569,620 B2 | 8/2009 | Muratoglu et al. |
| 7,595,074 B2 | 9/2009 | Cholli et al. |
| 7,615,075 B2 | 11/2009 | Kunze et al. |
| 7,635,725 B2 | 12/2009 | Bellare et al. |
| 7,683,133 B2 | 3/2010 | King et al. |
| 7,705,075 B2 | 4/2010 | Kumar et al. |
| 7,705,176 B2 | 4/2010 | Cholli et al. |
| 7,790,095 B2 | 9/2010 | Muratoglu et al. |
| 7,806,064 B2 | 10/2010 | Wellman |
| 7,833,452 B2 | 11/2010 | Muratoglu et al. |
| 7,846,376 B2 | 12/2010 | Abt et al. |
| 7,863,348 B2 | 1/2011 | Abt et al. |
| 8,129,440 B2 | 3/2012 | Rufner et al. |
| 8,178,594 B2 | 5/2012 | Rufner et al. |
| 8,399,535 B2 | 3/2013 | Pletcher |
| 8,470,903 B2 | 6/2013 | Abt et al. |
| 8,664,290 B2 | 3/2014 | Rufner et al. |
| 8,669,299 B2 | 3/2014 | Rufner et al. |
| 8,673,202 B2 | 3/2014 | Abt et al. |
| 2001/0027345 A1 | 10/2001 | Merrill et al. |
| 2001/0049401 A1 | 12/2001 | Salovey et al. |
| 2002/0007219 A1 | 1/2002 | Merrill et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0127778 A1 | 7/2003 | Scott et al. |
| 2003/0149125 A1 | 8/2003 | Muratoglu et al. |
| 2003/0158287 A1 | 8/2003 | Salovey et al. |
| 2003/0212161 A1 | 11/2003 | McKellop et al. |
| 2004/0051213 A1 | 3/2004 | Muratoglu et al. |
| 2004/0156879 A1 | 8/2004 | Muratoglu et al. |
| 2004/0265165 A1 | 12/2004 | King |
| 2005/0006821 A1 | 1/2005 | Merrill et al. |
| 2005/0056971 A1 | 3/2005 | Merrill et al. |
| 2005/0059750 A1 | 3/2005 | Sun et al. |
| 2005/0096749 A1 | 5/2005 | Merrill et al. |
| 2005/0124718 A1 | 6/2005 | Muratoglu et al. |
| 2005/0125074 A1 | 6/2005 | Salovey et al. |
| 2005/0146070 A1 | 7/2005 | Muratoglu et al. |
| 2005/0165495 A1 | 7/2005 | Merrill et al. |
| 2005/0194722 A1 | 9/2005 | Muratoglu et al. |
| 2005/0194723 A1 | 9/2005 | Muratoglu et al. |
| 2005/0267594 A1 | 12/2005 | Merrill et al. |
| 2006/0079597 A1 | 4/2006 | Muratoglu et al. |
| 2006/0115668 A1 | 6/2006 | King et al. |
| 2006/0264541 A1 | 11/2006 | Lederer et al. |
| 2007/0004818 A1 | 1/2007 | Muratoglu et al. |
| 2007/0043137 A1 | 2/2007 | Muratoglu et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0149660 A1 | 6/2007 | Kumar et al. |
| 2007/0191504 A1 | 8/2007 | Muratoglu |
| 2007/0232762 A1 | 10/2007 | Ernsberger et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2007/0293647 A1 | 12/2007 | McKellop et al. |
| 2008/0039545 A1 | 2/2008 | Muratoglu et al. |
| 2008/0067724 A1 | 3/2008 | Muratoglu et al. |
| 2008/0090933 A1 | 4/2008 | Muratoglu et al. |
| 2008/0090934 A1 | 4/2008 | Muratoglu et al. |
| 2008/0119582 A1 | 5/2008 | Muratoglu et al. |
| 2008/0133018 A1 | 6/2008 | Salovey et al. |
| 2008/0133021 A1 | 6/2008 | Shen et al. |
| 2008/0139137 A1 | 6/2008 | Guo et al. |
| 2008/0140196 A1 | 6/2008 | Schroeder et al. |
| 2008/0214692 A1 | 9/2008 | Muratoglu et al. |
| 2008/0215142 A1 | 9/2008 | Muratoglu et al. |
| 2008/0262120 A1 | 10/2008 | Muratoglu |
| 2008/0274161 A1 | 11/2008 | Muratoglu et al. |
| 2008/0293856 A1 | 11/2008 | Kumar et al. |
| 2008/0318022 A1 | 12/2008 | James et al. |
| 2008/0319137 A1 | 12/2008 | Rufner et al. |
| 2009/0030524 A1 | 1/2009 | Schroeder et al. |
| 2009/0105364 A1 | 4/2009 | Merrill et al. |
| 2009/0118390 A1 | 5/2009 | Abt et al. |
| 2009/0192610 A1 | 7/2009 | Case et al. |
| 2009/0265001 A1 | 10/2009 | Muratoglu et al. |
| 2009/0281624 A1 | 11/2009 | Conteduca et al. |
| 2010/0029858 A1 | 2/2010 | Rufner et al. |
| 2010/0082101 A1 | 4/2010 | Muratoglu et al. |
| 2010/0137481 A1 | 6/2010 | Shen et al. |
| 2010/0190882 A1 | 7/2010 | Muratoglu et al. |
| 2010/0331995 A1 | 12/2010 | Smelt et al. |
| 2011/0028600 A1 | 2/2011 | Rufner et al. |
| 2011/0306698 A1 | 12/2011 | Pletcher |
| 2012/0070600 A1 | 3/2012 | Muratoglu et al. |
| 2012/0157591 A1 | 6/2012 | Rufner et al. |
| 2014/0135415 A1 | 5/2014 | Abt et al. |
| 2014/0194934 A1 | 7/2014 | Rufner et al. |
| 2014/0194935 A1 | 7/2014 | Rufner et al. |

FOREIGN PATENT DOCUMENTS

| | | |
|---|---|---|
| EP | 0995449 A1 | 4/2000 |
| EP | 0560279 B1 | 6/2000 |
| EP | 0727195 B1 | 8/2002 |
| EP | 1421918 A1 | 5/2004 |
| EP | 1647242 A1 | 4/2006 |
| EP | 0935446 B1 | 2/2007 |
| EP | 1421918 B1 | 4/2008 |
| EP | 1647242 B1 | 5/2008 |
| EP | 1924614 A2 | 5/2008 |
| EP | 2046577 A1 | 4/2009 |
| EP | 2083981 A1 | 5/2009 |
| EP | 2150285 A2 | 2/2010 |
| EP | 2395048 A2 | 12/2011 |
| EP | 2150285 B1 | 2/2012 |
| EP | 2277560 B1 | 10/2013 |
| EP | 2395048 B1 | 10/2013 |
| EP | 2172229 B1 | 7/2014 |
| GB | 2288399 A | 10/1995 |
| JP | 11239611 A | 9/1999 |
| JP | 2006515777 A | 6/2006 |
| JP | 2009504283 A | 2/2009 |
| JP | 2009504898 A | 2/2009 |
| JP | 2009504897 A | 5/2009 |
| JP | 2010523805 A | 7/2010 |
| JP | 2012143575 A | 8/2012 |
| JP | 2015097814 A | 5/2015 |
| JP | 5735443 B2 | 6/2015 |
| KR | 20090035724 A | 4/2009 |
| WO | WO-8900755 A1 | 1/1989 |
| WO | WO-9729793 A1 | 8/1997 |
| WO | WO-9801085 A1 | 1/1998 |
| WO | WO-9814223 A1 | 4/1998 |
| WO | WO-0049079 A1 | 8/2000 |
| WO | WO-0105337 A1 | 1/2001 |
| WO | WO-0180778 A1 | 11/2001 |
| WO | WO-03049930 A1 | 6/2003 |
| WO | WO-2004024204 A1 | 3/2004 |
| WO | WO-2004064618 A2 | 8/2004 |
| WO | WO-2004064618 A3 | 8/2004 |
| WO | WO-2004101009 A1 | 11/2004 |
| WO | WO-2006041969 A1 | 4/2006 |
| WO | WO-2007019874 A1 | 2/2007 |
| WO | WO-2007024684 A2 | 3/2007 |
| WO | WO-2007024686 A3 | 3/2007 |
| WO | WO-2007056561 A2 | 5/2007 |
| WO | WO-2007121167 A1 | 10/2007 |

(56) References Cited

FOREIGN PATENT DOCUMENTS

| WO | WO-2008016174 A1 | 2/2008 |
|---|---|---|
| WO | WO-2008052574 A1 | 5/2008 |
| WO | WO-2008092047 A1 | 7/2008 |
| WO | WO-2008101073 A2 | 8/2008 |
| WO | WO-2008101134 A1 | 8/2008 |
| WO | WO-2008113388 A1 | 9/2008 |
| WO | WO-2008124825 A2 | 10/2008 |
| WO | WO-2008124825 A3 | 10/2008 |
| WO | WO-2009032909 A2 | 3/2009 |
| WO | WO-2009045658 A1 | 4/2009 |
| WO | WO-2009032909 A3 | 12/2009 |
| WO | WO-2010129514 A2 | 11/2010 |
| WO | WO-2010129514 A3 | 11/2010 |
| WO | WO-2015050851 A1 | 4/2015 |
| WO | WO-2015138137 A1 | 9/2015 |

OTHER PUBLICATIONS

"U.S. Appl. No. 11/465,743, Advisory Action mailed Jul. 16, 2008", 5 pgs.

"U.S. Appl. No. 11/465,743, Advisory Action mailed Aug. 6, 2008", 6 pgs.

"U.S. Appl. No. 11/465,743, Advisory Action mailed Aug. 24, 2009", 6 pgs.

"U.S. Appl. No. 11/465,743, Amended Appeal Brief filed Mar. 10, 2010", 42 pgs.

"U.S. Appl. No. 11/465,743, Amended Appeal Brief filed Dec. 15, 2009", 41 pgs.

"U.S. Appl. No. 11/465,743, Appeal Brief filed Nov. 15, 2009", 41 pgs.

"U.S. Appl. No. 11/465,743, Examiner Interview Summary mailed Apr. 29, 2009", 4 pgs.

"U.S. Appl. No. 11/465,743, Examiner Interview Summary mailed Sep. 23, 2010", 2 pgs.

"U.S. Appl. No. 11/465,743, Examiner Interview Summary mailed Sep. 29, 2010", 2 pgs.

"U.S. Appl. No. 11/465,743, Examiner Interview Summary mailed Oct. 31, 2008", 3 pgs.

"U.S. Appl. No. 11/465,743, Final Office Action mailed May 1, 2008", 9 pgs.

"U.S. Appl. No. 11/465,743, Final Office Action mailed Jun. 16, 2009", 11 pgs.

"U.S. Appl. No. 11/465,743, Non Final Office Action mailed Sep. 28, 2007", 7 pgs.

"U.S. Appl. No. 11/465,743, Non Final Office Action mailed Dec. 15, 2008", 12 pgs.

"U.S. Appl. No. 11/465,743, Notice of Allowance mailed May 26, 2010", 6 pgs.

"U.S. Appl. No. 11/465,743, Notice of Allowance mailed Sep. 3, 2010", 7 pgs.

"U.S. Appl. No. 11/465,743, Response filed Jan. 17, 2008 to Non Final Office Action mailed Sep. 28, 2007", 13 pgs.

"U.S. Appl. No. 11/465,743, Response filed Feb. 16, 2009 to Non Final Office Action mailed Dec. 15, 2008", 11 pgs.

"U.S. Appl. No. 11/465,743, Response filed Jul. 1, 2008 to Final Office Action mailed May 1, 2008", 8 pgs.

"U.S. Appl. No. 11/465,743, Response filed Jul. 22, 2008 to Advisory Action mailed Jul. 16, 2008", 6 pgs.

"U.S. Appl. No. 11/465,743, Response filed Jul. 29, 2009 to Final Office Action mailed Jun. 16, 2009", 15 pgs.

"U.S. Appl. No. 11/465,743, Response filed Oct. 31, 2008 to Advisory Action mailed Aug. 6, 2008", 15 pgs.

"U.S. Appl. No. 11/465,743, Supplemental Notice of Allowability mailed Jul. 14, 2010", 2 pgs.

"U.S. Appl. No. 11/465,743, Supplemental Notice of Allowability mailed Sep. 23, 2010", 4 pgs.

"U.S. Appl. No. 11/465,743, Supplemental Notice of Allowability mailed Sep. 29, 2010", 4 pgs.

"U.S. Appl. No. 11/465,743, Supplemental Response filed Apr. 20, 2009 to Non Final Office Action mailed Dec. 15, 2008", 10 pgs.

"U.S. Appl. No. 12/100,894, Examiner Interview Summary mailed Dec. 2, 2009", 3 pgs.

"U.S. Appl. No. 12/100,894, Non Final Office Action mailed Apr. 14, 2009", 16 pgs.

"U.S. Appl. No. 12/100,894, Response filed Mar. 31, 2009 to Restriction Requirement mailed Mar. 2, 2009", 2 pgs.

"U.S. Appl. No. 12/100,894, Restriction Requirement mailed Mar. 2, 2009", 7 pgs.

"U.S. Appl. No. 12/262,531, Final Office Action mailed Jan. 14, 2010", 11 pgs.

"U.S. Appl. No. 12/262,531, Non Final Office Action mailed Jun. 17, 2010", 16 pgs.

"U.S. Appl. No. 12/262,531, Non Final Office Action mailed Jun. 25, 2009", 7 pgs.

"U.S. Appl. No. 12/262,531, Notice of Allowance mailed Oct. 28, 2010", 6 pgs.

"U.S. Appl. No. 12/262,531, Preliminary Amendment filed Oct. 31, 2008", 6 pgs.

"U.S. Appl. No. 12/262,531, Response filed Apr. 28, 2010 to Final Office Action mailed Jan. 14, 2010", 15 pgs.

"U.S. Appl. No. 12/262,531, Response filed Sep. 17, 2010 to Non Final Office Action mailed Jun. 17, 2010", 4 pgs.

"U.S. Appl. No. 12/262,531, Response filed Sep. 23, 2009 to Non Final Office Action mailed Jun. 25, 2009", 10 pgs.

"U.S. Appl. No. 12/262,531, Supplemental Notice of Allowability mailed Nov. 23, 2010", 4 pgs.

"U.S. Appl. No. 12/464,235, Final Office Action mailed Aug. 19, 2010", 11 pgs.

"U.S. Appl. No. 12/464,235, Non Final Office Action mailed Mar. 2, 2010", 7 pgs.

"U.S. Appl. No. 12/464,235, Non Final Office Action mailed Dec. 23, 2010", 10 pgs.

"U.S. Appl. No. 12/579,094, Examiner Interview Summary mailed Jan. 6, 2012", 1 pg.

"U.S. Appl. No. 12/579,094, Final Office Action mailed Oct. 13, 2010", 14 pgs.

"U.S. Appl. No. 12/579,094, Non Final Office Action mailed May 18, 2010", 19 pgs.

"U.S. Appl. No. 12/579,094, Notice of Allowance mailed Jan. 6, 2012", 8 pgs.

"U.S. Appl. No. 12/579,094, Preliminary Amendment filed Oct. 14, 2009", 11 pgs.

"U.S. Appl. No. 12/579,094, Response filed Jan. 27, 2012 to Notice of Allowance mailed Jan. 6, 2012", 5 pgs.

"U.S. Appl. No. 12/579,094, Response filed Jan. 31, 2012 to 312 Amendment mailed Jan. 27, 2012", 2 pgs.

"U.S. Appl. No. 12/579,094, Response filed Apr. 7, 2010 to Restriction Requirement mailed Mar. 9, 2010", 9 pgs.

"U.S. Appl. No. 12/579,094, Response filed Apr. 12, 2011 to Final Office Action mailed Oct. 13, 2010", 45 pgs.

"U.S. Appl. No. 12/579,094, Response filed Sep. 20, 2010 to Non Final Office Action mailed May 18, 2010", 30 pgs.

"U.S. Appl. No. 12/579,094, Restriction Requirement mailed Mar. 9, 2010", 7 pgs.

"U.S. Appl. No. 12/813,401, Non Final Office Action mailed Aug. 14, 2012", 10 pgs.

"U.S. Appl. No. 12/813,401, Non Final Office Action mailed Aug. 26, 2011", 9 pgs.

"U.S. Appl. No. 12/813,401, Notice of Allowance mailed Apr. 16, 2012", 7 pgs.

"U.S. Appl. No. 12/813,401, Notice of Allowance mailed Nov. 21, 2012", 5 pgs.

"U.S. Appl. No. 12/813,401, Response filed Jan. 26, 2012 to Non Final Office Action mailed Aug. 26, 2011", 7 pgs.

"U.S. Appl. No. 12/813,401, Response filed Oct. 26, 2012 to Non Final Office Action mailed Aug. 14, 2012", 8 pgs.

"U.S. Appl. No. 12/847,741, Examiner Interview Summary mailed Aug. 6, 2013", 4 pgs.

"U.S. Appl. No. 12/847,741, Final Office Action mailed Jun. 27, 2012", 7 pgs.

(56) References Cited

OTHER PUBLICATIONS

"U.S. Appl. No. 12/847,741, Non Final Office Action mailed Feb. 24, 2012", 11 pgs.
"U.S. Appl. No. 12/847,741, Non Final Office Action mailed May 9, 2013", 11 pgs.
"U.S. Appl. No. 12/847,741, Notice of Allowance mailed Oct. 17, 2013", 11 pgs.
"U.S. Appl. No. 12/847,741, Preliminary Amendment filed Oct. 18, 2010", 5 pgs.
"U.S. Appl. No. 12/847,741, Response filed May 23, 2012 to Non Final Office Action mailed Feb. 24, 2012", 10 pgs.
"U.S. Appl. No. 12/847,741, Response filed Sep. 3, 2013 to Non Final Office Action mailed May 9, 2013", 18 pgs.
"U.S. Appl. No. 12/847,741, Response filed Sep. 26, 2012 to Final Office Action mailed Jun. 27, 2012", 14 pgs.
"U.S. Appl. No. 12/847,741, Second Preliminary Amendment filed Feb. 21, 2012", 4 pgs.
"U.S. Appl. No. 12/942,703, Applicant's Summary of Examiner Interview filed Feb. 17, 2012", 3 pgs.
"U.S. Appl. No. 12/942,703, Final Office Action mailed Jan. 7, 2013", 8 pgs.
"U.S. Appl. No. 12/942,703, Final Office Action mailed Mar. 16, 2012", 14 pgs.
"U.S. Appl. No. 12/942,703, Non Final Office Action mailed Aug. 2, 2011", 17 pgs.
"U.S. Appl. No. 12/942,703, Non Final Office Action mailed Aug. 23, 2012", 14 pgs.
"U.S. Appl. No. 12/942,703, Notice of Allowance mailed Mar. 1, 2013", 8 pgs.
"U.S. Appl. No. 12/942,703, Response filed Jan. 3, 2012 to Non Final Office Action mailed Aug. 2, 2011", 34 pgs.
"U.S. Appl. No. 12/942,703, Response filed Feb. 13, 2013 to Final Office Action mailed Jan. 7, 2013", 7 pgs.
"U.S. Appl. No. 12/942,703, Response filed Jul. 16, 2012 to Final Office Action mailed Mar. 16, 2012", 14 pgs.
"U.S. Appl. No. 12/942,703, Response filed Nov. 30, 2012 to Non Final Office Action mailed Aug. 23, 2012", 15 pgs.
"U.S. Appl. No. 12/943,160, Applicant's Summary of Examiner Interview filed Feb. 17, 2012", 2 pgs.
"U.S. Appl. No. 12/943,160, Examiner Interview Summary mailed Feb. 2, 2012", 2 pgs.
"U.S. Appl. No. 12/943,160, Examiner Interview Summary mailed Aug. 15, 2013", 3 pgs.
"U.S. Appl. No. 12/943,160, Final Office Action mailed Sep. 28, 2012", 14 pgs.
"U.S. Appl. No. 12/943,160, Non Final Office Action mailed Mar. 16, 2012", 11 pgs.
"U.S. Appl. No. 12/943,160, Non Final Office Action mailed Jun. 26, 2013", 9 pgs.
"U.S. Appl. No. 12/943,160, Non Final Office Action mailed Aug. 12, 2011", 8 pgs.
"U.S. Appl. No. 12/943,160, Notice of Allowance mailed Oct. 17, 2013", 9 pgs.
"U.S. Appl. No. 12/943,160, Response filed Jan. 11, 2012 to Non Final Office Action mailed Aug. 12, 2011", 13 pgs.
"U.S. Appl. No. 12/943,160, Response filed Jul. 16, 2012 to Non Final Office Action mailed Mar. 16, 2012", 13 pgs.
"U.S. Appl. No. 12/943,160, Response filed Sep. 18, 2013 to Non Final Office Action mailed Jun. 26, 2013", 8 pgs.
"U.S. Appl. No. 12/943,160, Response filed Nov. 20, 2012 to Non Final Office Action mailed Sep. 28, 2012", 10 pgs.
"U.S. Appl. No. 12/967,581, Examiner Interview Summary mailed Jan. 23, 2012", 2 pgs.
"U.S. Appl. No. 12/967,581, Notice of Allowance mailed Feb. 7, 2012", 10 pgs.
"U.S. Appl. No. 12/967,581, Preliminary Amendment filed Jan. 19, 2012", 7 pgs.
"U.S. Appl. No. 12/967,581, Preliminary Amendment filed Jan. 27, 2012", 4 pgs.
"U.S. Appl. No. 12/967,581, Preliminary Amendment filed Feb. 18, 2011", 5 pgs.
"U.S. Appl. No. 12/967,581, Preliminary Amendment filed Dec. 14, 2010", 7 pgs.
"U.S. Appl. No. 13/403,040, Advisory Action mailed Jan. 28, 2013", 6 pgs.
"U.S. Appl. No. 13/403,040, Examiner Interview Summary mailed Jan. 30, 2013", 3 pgs.
"U.S. Appl. No. 13/403,040, Final Office Action mailed Nov. 19, 2012", 14 pgs.
"U.S. Appl. No. 13/403,040, Non Final Office Action mailed Jul. 1, 2013", 8 pgs.
"U.S. Appl. No. 13/403,040, Non Final Office Action mailed Jul. 16, 2012", 14 pgs.
"U.S. Appl. No. 13/403,040, Notice of Allowance mailed Oct. 16, 2013", 10 pgs.
"U.S. Appl. No. 13/403,040, PTO Response to 312 Amendment mailed Feb. 6, 2014", 2 pgs.
"U.S. Appl. No. 13/403,040, Response filed Jan. 22, 2013 to Final Office Action mailed Nov. 19, 2012", 13 pgs.
"U.S. Appl. No. 13/403,040, Response filed Feb. 18, 2013 to Advisory Action mailed Jan. 28, 2013", 13 pgs.
"U.S. Appl. No. 13/403,040, Response filed Sep. 3, 2013 to Non Final Office Action mailed Jul. 1, 2013", 13 pgs.
"U.S. Appl. No. 13/403,040, Response filed Oct. 16, 2012 to Non Final Office Action mailed Jul. 16, 2012", 15 pgs.
"U.S. Appl. No. 14/157,687, Non Final Office Action mailed Oct. 8, 2015", 20 pgs.
"U.S. Appl. No. 14/157,687, Preliminary Amendment mailed Jan. 22, 2014", 6 pgs.
"U.S. Appl. No. 14/157,687, Response filed Jan. 6, 2016 to Non Final Office Action mailed Oct. 8, 2015", 15 pgs.
"U.S. Appl. No. 14/157,695, Final Office Action mailed Sep. 2, 2015", 13 pgs.
"U.S. Appl. No. 14/157,695, Non Final Office Action mailed May 8, 2015", 16 pgs.
"U.S. Appl. No. 14/157,695, Notice of Allowance mailed Sep. 23, 2015", 9 pgs.
"U.S. Appl. No. 14/157,695, Preliminary Amendment filed Jan. 29, 2014", 21 pgs.
"U.S. Appl. No. 14/157,695, Response filed Aug. 7, 2015 to Non Final Office Action mailed May 8, 2015", 18 pgs.
"U.S. Appl. No. 14/157,695, Response filed Sep. 10, 2015 to Final Office Action mailed Sep. 2, 2015", 12 pgs.
"U.S. Appl. No. 14/157,708, Non Final Office Action mailed Jun. 10, 2015", 15 pgs.
"U.S. Appl. No. 14/157,708, Notice of Allowance mailed Oct. 14, 2015", 9 pgs.
"U.S. Appl. No. 14/157,708, Preliminary Amendment mailed Jan. 22, 2014", 18 pgs.
"U.S. Appl. No. 14/157,708, Response filed Sep. 10, 2015 to Non Final Office Action mailed Jun. 10, 2015", 17 pgs.
"U.S. Appl. No. 14/978,598, Preliminary Amendment filed Dec. 28, 2015", 5 pgs.
"U.S. Appl. No. 14/983,006, Preliminary Amendment filed Dec. 30, 2015", 5 pgs.
"Australian Application Serial No. 2005335669, Office Action mailed Mar. 21, 2011", 3 pgs.
"Australian Application Serial No. 2005335669, Response filed Feb. 1, 2012 to Office Action mailed Mar. 21, 2011", 15 pgs.
"Australian Application Serial No. 2008236996, Office Action mailed Jun. 19, 2012", 3 pgs.
"Australian Application Serial No. 2012203503, First Examiner Report mailed May 7, 2013", 4 pgs.
"Australian Application Serial No. 2012203503, Response filed Sep. 24, 2013 to First Examiner Report mailed May 7, 2013", 17 pgs.
"Australian Application Serial No. 2013200780, First Examiner Report mailed Jan. 3, 2014", 3 pgs.
"Australian Application Serial No. 2013200780, Response filed Apr. 9, 2014 to First Examiner Report mailed Jan. 3, 2014", 28 pgs.
"Australian Application Serial No. 2013200780, Response filed Aug. 5, 2014 to Office Action mailed May 22, 2014", 3 pgs.

(56) References Cited

OTHER PUBLICATIONS

"Australian Application Serial No. 2013200780, Subsequent Examiners Report mailed May 22, 2014", 3 pgs.
"Australian Application Serial No. 2013200780, Subsequent Examiners Report mailed Sep. 3, 2014", 3 pgs.
"Biomet Orthopedics", Brochure E-POL Y HSLPE (EXH20), (2007), 23 pgs.
"Canadian Application No. 2,619,502, Office Action mailed Nov. 4, 2011", 4 pgs.
"Canadian Application No. 2,619,502, Response filed Jan. 30, 2012 to Office Action mailed Nov. 4, 2011", 6 pgs.
"Canadian Application No. 2,619,502, Response filed Sep. 2, 2011 to Office Action mailed Nov. 4, 2011", 17 pgs.
"Canadian Application Serial 2,678,459, Office Action mailed Jul. 23, 2015", 4 pgs.
"Canadian Application Serial No. 2,678,459, Office Action mailed Apr. 11, 2013", 4 pgs.
"Canadian Application Serial No. 2,678,459, Office Action mailed Nov. 21, 2014", 2 pgs.
"Canadian Application Serial No. 2,678,459, Response filed Mar. 25, 2015 to Office Action mailed Nov. 21, 2014", 57 pgs.
"Canadian Application Serial No. 2,678,459, Response filed Oct. 11, 2013 to Office Action mailed Apr. 11, 2013", 45 pgs.
"Canadian Application Serial No. 2,788,687, Office Action mailed Jun. 4, 2014", 2 pgs.
"Canadian Application Serial No. 2,788,687, Office Action mailed Jul. 10, 2013", 4 pgs.
"Canadian Application Serial No. 2,788,687, Office Action mailed Aug. 27, 2015", 4 pgs.
"Canadian Application Serial No. 2,788,687, Response filed Jul. 10, 2013 to Office Action mailed Jan. 10, 2014", 25 pgs.
"E-POLY HXLPE Brochure", Biomet Orthopedics, (2007), 23 pgs.
"European Application Serial No. 05777319.4, Office Action mailed Jun. 10, 2009", 4 pgs.
"European Application Serial No. 05777319.4, Office Action mailed Jul. 28, 2010", 1 pg.
"European Application Serial No. 05777319.4, Office Action mailed Sep. 15, 2008", 1 pg.
"European Application Serial No. 05777319.4, Response filed Jan. 20, 2009 to Office Action mailed Sep. 15, 2008", 7 pgs.
"European Application Serial No. 05777319.4, Response filed Oct. 8, 2009 to Office Action mailed Jun. 10, 2009", 9 pgs.
"European Application Serial No. 08745507.7, Office Action mailed Jan. 12, 2010", 2 pgs.
"European Application Serial No. 08745507.7, Office Action mailed May 10, 2010", 3 pgs.
"European Application Serial No. 08745507.7, Office Action mailed Jul. 20, 2011", 4 pgs.
"European Application Serial No. 08745507.7, Office Action mailed Dec. 12, 2012", 1 pg.
"European Application Serial No. 08745507.7, Response filed Feb. 16, 2010 to Office Action mailed Jan. 12, 2010", 5 pgs.
"European Application Serial No. 08745507.7, Response filed Sep. 20, 2010 to Office Action mailed May 10, 2010", 3 pgs.
"European Application Serial No. 08745507.7, Response filed Nov. 21, 2011 to Office Action mailed Jul. 20, 2011", 3 pgs.
"European Application Serial No. 09013154.1, European Examination Notification mailed Jan. 4, 2013", 4 pgs.
"European Application Serial No. 09013154.1, European Search Report mailed Feb. 23, 2010", 6 pgs.
"European Application Serial No. 09013154.1, Office Action mailed Sep. 14, 2011", 4 pgs.
"European Application Serial No. 09013154.1, Office Action mailed Oct. 21, 2010", 1 pg.
"European Application Serial No. 09013154.1, Response filed Jan. 26, 2012 to Office Action mailed Sep. 14, 2011", 7 pgs.
"European Application Serial No. 09013154.1, Response filed Mar. 21, 2011 to Office Action mailed Oct. 21, 2010", 22 pgs.
"European Application Serial No. 09013154.1, Response filed May 14, 2013 to Examination Notification Art. 94(3) mailed Jan. 4, 2013", 9 pgs.
"European Application Serial No. 10012579.8, European Search Report mailed Feb. 23, 2010", 3 pgs.
"European Application Serial No. 10012579.8, Extended Search Report and Written Opinion mailed Dec. 9, 2010", 8 pgs.
"European Application Serial No. 10012579.8, Extended Search Report and Written Opinion mailed Dec. 16, 2010", 8 pgs.
"European Application Serial No. 10012579.8, Notice of Opposition mailed Aug. 18, 2014", 1 pg.
"European Application Serial No. 10012579.8, Office Action mailed Jan. 31, 2011", 2 pgs.
"European Application Serial No. 10012579.8, Office Action mailed Apr. 23, 2012", 4 pgs.
"European Application Serial No. 10012579.8, Office Action mailed Sep. 14, 2011", 4 pgs.
"European Application Serial No. 10012579.8, Office Action mailed Sep. 18, 2012", 4 pgs.
"European Application Serial No. 10012579.8, Response filed Jan. 26, 2012 to Office Action mailed Sep. 14, 2011", 11 pgs.
"European Application Serial No. 10012579.8, Response filed Jan. 28, 2013 to Examination Notification Art. 94(3) mailed Sep. 18, 2012", 9 pgs.
"European Application Serial No. 10012579.8, Response filed Jul. 3, 2012 to Office Action mailed Apr. 23, 2012", 15 pgs.
"European Application Serial No. 10012579.8, Response filed Jul. 26, 2011 to Office Action mailed Jan. 31, 2011", 29 pgs.
"European Application Serial No. 10012589.7, European Search Report mailed Feb. 23, 2010", 6 pgs.
"European Application Serial No. 10012589.7, European Search Report mailed Dec. 9, 2010", 7 pgs.
"European Application Serial No. 10012589.7, Extended Search Report and Written Opinion mailed Dec. 16, 2010", 8 pgs.
"European Application Serial No. 10012589.7, Office Action mailed Jan. 31, 2011", 2 pgs.
"European Application Serial No. 10012589.7, Office Action mailed Feb. 3, 2010", 1 pg.
"European Application Serial No. 10012589.7, Office Action mailed Mar. 27, 2012", 4 pgs.
"European Application Serial No. 10012589.7, Office Action mailed Dec. 16, 2010", 1 pg.
"European Application Serial No. 10012589.7, Response filed Jan. 13, 2012", 8 pgs.
"European Application Serial No. 10012589.7, Response filed Feb. 13, 2012 to Office Action mailed Dec. 2, 2011", 7 pgs.
"European Application Serial No. 10012589.7, Response filed Jul. 26, 2011 to Office Action mailed Jan. 31, 2011", 9 pgs.
"European Application Serial No. 11169368.5, European Search Report mailed Apr. 23, 2012", 5 pgs.
"European Application Serial No. 11169368.5, Response filed Nov. 1, 2012 to European Search Report mailed Apr. 23, 2012", 9 pgs.
"European Application Serial No. 12154330.0, European Search Report mailed Jul. 18, 2012", 15 pgs.
"European Application Serial No. 12154330.0, Examination Notification Art. 94(3) mailed Mar. 10, 2015", 10 pgs.
"European Application Serial No. 12154330.0, Examination Notification Art. 94(3) mailed May 30, 2013", 11 pgs.
"European Application Serial No. 12154330.0, Examination Notification Art. 94(3) mailed Aug. 7, 2013", 9 pgs.
"European Application Serial No. 12154330.0, Response filed Feb. 15, 2013 to Extended European Search Report mailed Jul. 18, 2012", 18 pgs.
"European Application Serial No. 12154330.0, Response filed Jul. 3, 2013 to Examination Notification Art. 94(3) mailed May 30, 2013", 8 pgs.
"European Application Serial No. 12154330.0, Response filed Dec. 17, 2013 to Examination Notification Art. 94(3) mailed Aug. 7, 2013", 14 pgs.
"European Application Serial No. 12167580.5, Examination Notification Art. 94(3) mailed Mar. 26, 2015", 3 pgs.
"European Application Serial No. 12167580.5, Extended European Search Report mailed Feb. 4, 2013", 15 pgs.

(56) References Cited

OTHER PUBLICATIONS

"European Application Serial No. 12167580.5, Response filed Aug. 5, 2015 Examination Notification Art. 94(3) mailed Mar. 26, 2015", 9 pgs.
"European Application Serial No. 12167580.5, Response filed Sep. 5, 2013 to Extended European Search Report mailed Feb. 4, 2013", 18 pgs.
"European Application Serial No. 12167581.3, European Search Report mailed Mar. 13, 2013", 13 pgs.
"European Application Serial No. 12167581.3, Examination Notification Art. 94(3) mailed Mar. 26, 2015", 4 pgs.
"European Application Serial No. 12167581.3, Response filed Aug. 5, 2015 to Examination Notification Art. 94(3) mailed Mar. 26, 2015", 14 pgs.
"European Application Serial No. 12167581.3, Response filed Oct. 10, 2013 to Extended European Search Report mailed Mar. 13, 2013", 16 pgs.
"European Application Serial No. 14173530.8, Extended European Search Report mailed Sep. 24, 2014", 8 pgs.
"International Application Serial No. PCT/EP2005/008967, International Preliminary Report on Patentability mailed Feb. 20, 2008", 7 pgs.
"International Application Serial No. PCT/EP2005/008967, International Search Report and Written Opinion mailed Jun. 21, 2006", 10 pgs.
"International Application Serial No. PCT/EP2009/008250, International Search Report mailed Jan. 21, 2010", 3 pgs.
"International Application Serial No. PCT/EP2009/008250, Written Opinion mailed Jan. 21, 2010", 5 pgs.
"International Application Serial No. PCT/US2008/059909, International Preliminary Report on Patentability mailed Nov. 10, 2009", 8 pgs.
"International Application Serial No. PCT/US2008/059909, International Search Report and Written Opinion mailed Sep. 14, 2009", 14 pgs.
"International Application Serial No. PCT/US2008/086817, International Search Report mailed Sep. 14, 2009", 3 pgs.
"International Application Serial No. PCT/US2008/086817, Written Opinion mailed Sep. 14, 2009", 7 pgs.
"International Application Serial No. PCT/US2009/032412, International Search Report and Written Opinion mailed Mar. 25, 2010", 9 pgs.
"International Application Serial No. PCT/US2014/058241, International Search Report mailed Nov. 27, 2014", 3 pgs.
"International Application Serial No. PCT/US2014/058241, Written Opinion mailed Nov. 27, 2014", 3 pgs.
"International Application Serial No. PCT/US2015/017741, International Search Report mailed Aug. 7, 2015", 5 pgs.
"International Application Serial No. PCT/US2015/017741, Written Opinion mailed Aug. 7, 2015", 7 pgs.
"Japanese Application Serial No. 2008-526378, Office Action mailed Jun. 19, 2012", (w/ English translation), 6 pgs.
"Japanese Application Serial No. 2008-526378, Office Action mailed Sep. 6, 2011", (w/ English Translation), 11 pgs.
"Japanese Application Serial No. 2008-526378, Office Action mailed Dec. 18, 2012", (w/ English translation), 4 pgs.
"Japanese Application Serial No. 2008-526378, Response filed Mar. 6, 2012 to Office Action mailed Sep. 6, 2011", (w/ English translation of claims), 10 pgs.
"Japanese Application Serial No. 2008-526378, Response filed May 28, 2013 to Office Action mailed Dec. 18, 2012", (w/ English translation of claims), 8 pgs.
"Japanese Application Serial No. 2008-526378, Response filed Oct. 19, 2012 to Examiners Decision of Final Refusal mailed Jun. 19, 2012", (w/ English translation of claims), 13 pgs.
"Japanese Application Serial No. 2010-503206, Examiners Decision of Final Refusal mailed May 7, 2013", (w/ English translation), 5 pgs.
"Japanese Application Serial No. 2010-503206, Office Action mailed Dec. 4, 2012", (w/ English translation), 7 pgs.
"Japanese Application Serial No. 2010-503206, Response filed Mar. 4, 2013 to Office Action mailed Dec. 4, 2012", (w/ English translation), 13 pgs.
"Japanese Application Serial No. 2012-049675, Examiners Decision of Final Refusal mailed Sep. 30, 2014", (W/ English Translation), 9 pgs.
"Japanese Application Serial No. 2012-049675, Office Action mailed Jan. 30, 2015", (w/ English translation of claims), 16 pgs.
"Japanese Application Serial No. 2012-049675, Office Action mailed Sep. 3, 2013", (w/ English translation), 13 pgs.
"Japanese Application Serial No. 2012-049675, Response filed Feb. 28, 2014 to Office Action mailed Sep. 3, 2013", (W/ English Translation), 14 pgs.
"Japanese Application Serial No. 2015-016315, Amendment filed Feb. 26, 2015", (W/ English Translation), 8 pgs.
"Japanese Application Serial No. 2015-016315, Office Action mailed Dec. 8, 2015", With English translation, 13 pgs.
"Joint Replacement Material Developed at the Massachusetts General Hospital", from MA General Hosp. MGH Hotline On-line publication, (Aug. 10, 2007), 1 pg.
"JP 11-239611A, English Translation", 10 pgs.
"New joint replacement material developed at Massachusetts General Hospital and put to first clinic use", news release from Massachusetts General Hospital, accessed May 13, 2008, (Nov. 15, 2010), 2 pgs.
"Opposition Application No. 09013154.1, Opposition Brief filed Apr. 16, 2014", (w/ English Translation), 22 pgs.
"Opposition to EP 2277560, Notice of Opposition filed on Jul. 4, 2014", 14 pgs.
"Opposition to EP 2277560, Response filed Feb. 26, 2015 to Notice of Opposition filed on Jul. 4, 2014", 12 pgs.
"Prevention of Fatigue Cracks in Ultrahigh Morecular Weight Polyethylene Joint Components by the Addition of Vitamin E", J. Biomed. Mater. Res., vol. 48,, (1999), 474-478.
"Studies on the effect of electron beam radiation on the molecular structure of ultra-high molecularweight polyethylene under the influence of a-tocopherol with respect to its application in medical implants", J. Materials Science: Materials in Medicine, vol. 13, No. 10, (2002), 917-921.
"The anti-oxidative properties of a-tocopherol in y-irradiated UHMWPE with respect to fatigue and oxidation resistance", Biomatyerials, vol. 26, (Apr. 1, 2005), 5755-5762.
Badertscher, R. P., et al., "Grafting of a-tocopherol upon y-irradiation UHMWPE probed by model hydrocarbons", Polymer Degradation and Stability, 97, (2012), 2255-2261.
Bauer, I., et al., "Antioxidant interaction between organic phosphites and hindered amine light stabilisers during processing and thermoxidation of polypropylene", Polymer Degradation and Stability, 48(3), (1995), 427-440.
Bauer, I., et al., "Antioxidant interaction between organic phosphites and hindered amine light stabilizers: effects during photoxidation of polypropylene—II", Polymer Degradation and Stability, 55(2), (1997), 217-224.
Bauer, I., et al., "Hydroperoxide decomposing ability and hydrolytic stability of organic phosphites containing hindered amine moieties (HALS-Phosphites)", Polymer Degradation and Stability, 62(1), (1998), 175-186.
Bragdon, et al., "A New Pin-on-disk wear testing method for simulating wear of polyethylene on cobalt-chrome alloy in total hip arthroplasty", The Journal of Arthroplasty vol. 16, No. 5, (2001), 658-665.
Chmela, S., et al., "HALS-phosphite combinations as light and heat stabilizers for polypropylene", Polymer Degradation and Stability, 39(3), (1993), 367-371.
Davidson, Ernesto, et al., "Characterization of UHMWPE Irradiated with gamma rays stored in E vitamin and thermally treated", Revista De La Facultad De Ingenieria Universidad Central De Venezuela, 26(1),, (2011), 7 pgs.
Greer, K. W., et al., "The Effects of Raw Material, Irradiation Dose, and Irradiation Source on Crosslinking of UHMWPE", Journal of ASTM International, vol. 1, No. 1, (Jan. 2004), pp. 1-11.

(56) References Cited

OTHER PUBLICATIONS

Habicher, Wolf D, et al., "Synthesis and antioxidative properties of novel multifunctional stabilizers", Journal of Vinyl and Additive Technology, 7(1), (Mar. 2001), 4-18.

Hahner, U., et al., "Synthesis and antioxidative efficiency of organic phosphites and phosphonites with 2.2.6.6-tetramethylpiperidin-4-yl groups", Polymer Degradation and Stability, 41(2), (1993), 197-203.

Ingo, John, "Evaluation of cross-linked UHMWPE with regards to its suitability as implant material for hip joint shells", Series: Plastics Research published by Manfred H. Wagner, Translation, (2003), 28 pgs.

Kurtz, S, et al., "Trace Concentrations of Vitamin E Protect Radiation Crosslinked UHMWPE from Oxidative Degradation", 53rd Annual Meeting of the Orthopaedic Research Society,.Feb. Paper No. 0020, (Nov. 14, 2007), 1 pg.

Muratoglu, Orhun K., et al., "A Novel Method of Cross-Linking Ultra-High-Molecular-Weight Polyethylene to Improve Wear, Reduce Oxidation, and Retain Mechanical Properties", The Journal of Arthroplasty, vol. 16, No. 2, (2001), 149-160.

Muratoglu, Orhun K, et al., "Larger Diameter Femoral Heads Used in Conjunction With a Highly Cross-Linked Ultra-High Molecular Weight Polyethylene: A New Concept", The Journal of Arthoplasty 16(8) Suppl. 1, (2001), 24-30.

Oral, et al., "Alpha-Tocopherol-doped irradiated UHMWPE for high fatigue resistance and low wear", Biomaterials vol. 25, (2004), 5515-5522.

Oral, et al., "Blending a-Tocopherol with UHMWPE Powder for Oxidation Resistance", Poster 1485, 50th Annual Meeting of Orthopaedic Research Society, San Francisco CA, Mar. 7-10, 2004, Transactions, vol. 29, (2004), 1 pg.

Oral, E, et al., "Characterization of irradiated blends of alpha-tocopherol and UHMWPE", Biomaterials, 26(33), (Nov. 2005), 6657-6663.

Oral, E, et al., "Crosslinked Vitamin E Blended UHMWPE with Improved Grafting and Wear Resistance", ORS Annual Meeting, Poster No. 1181, (2011), 1 pg.

Oral, E, et al., "Trace amounts of grafted vitamin E protect UHMWPE against squalene-initiated oxidation", ORS Annual Meeting, Poster No. 1295, (2011), 1 pg.

Parth, M., et al., "Studies on the effect of electron beam radiation on the molecular structure of ultra-high molecular weight polyethylene under the influence of a-tocopherol with respect to its application in medical implants", Journal of Materials Science: Materials in Medicine, 13(10), (2002), 917-921.

Pletcher, Dirk, et al., "Polymers Compositions Including an Antioxidant", U.S. Appl. No. 12/813,401, filed Jun. 10, 2010, 52 pgs.

Rowell, S, et al., "Detection of Vitamin E in Irradiated UHMWPE by UV-Visible Spectroscopy", ORS 2011 Annual Meeting, Poster No. 1186, (2011), 1 pg.

Rufner, Alicia, et al., "An Antioxidant Stabilized Crosslinked Ultra-High Molecular Weight Polyethylene for Medical Device Applications", U.S. Appl. No. 12/847,741, filed Jul. 30, 2010, 69 pgs.

Shibata, N, et al., "The anti-oxidative properties of alpha-tocopherol in gamma-irradiated UHMWPE with respect to fatigue and oxidation resistance", Biomaterials, 26(29), (Apr. 19, 2005), 5755-5762.

Tomita, N., et al., "Prevention of fatigue cracks in ultrahigh molecular weight polyethylene joint components by the addition of vitamin E", J Biomed Mater Res., 48(4), (1999), 474-478.

Wagner, Manfred H., "Evaluation of cross-linked UHMWPE with regards to its suitability as implant material for hip joint shells", (w/ English Translation), Plastics Research, 56, (2003), 95 pgs.

Wannomae, et al., "Vitamin E Stabilized, Irradiated UHMWPE for Cruciate Retaining Knee Components", 53rd Annual Meeting of the Orthopaedic Research Society, Poster No. 1783, (Nov. 14, 2007), 1 pg.

Wolf, C, et al., "Radiation Grafting of Vitamin E to Ultra High Molecular Weight Polyethylene", ORS Annual Meeting, Poster No. 1178, (2011), 1 pg.

POLYMER COMPOSITIONS COMPRISING ONE OR MORE PROTECTED ANTIOXIDANTS

CROSS-REFERENCE TO RELATED APPLICATIONS

This application is a U.S. National Stage Application under 35 U.S.C. 371 from International Application No. PCT/US2014/058241, filed Sep. 30, 2014, and published as WO 2015/050851A1 on Apr. 9, 2015, which claims the benefit of U.S. Provisional Patent Application Ser. No. 61/885,316, filed Oct. 1, 2013, the benefit of priority of each of which is claimed hereby, and each of which are incorporated by reference herein in its entirety.

BACKGROUND OF THE INVENTION

Many endoprosthetic joint replacements currently implanted in patients include a highly polished metal or ceramic component articulating on an ultra high molecular weight polyethylene (UHMWPE) material. Wear and abrasion resistance, coefficient of friction, impact strength, toughness, density, biocompatibility, and biostability are some of the properties that make UHMWPE a suitable material for such implants. Although UHMWPE has been used in implants for many years, there is continuing interest in the wear and durability characteristics of implants incorporating UHMWPE.

SUMMARY OF THE INVENTION

In some embodiments, the invention relates to protected antioxidants of the formula (I) or (Ib):

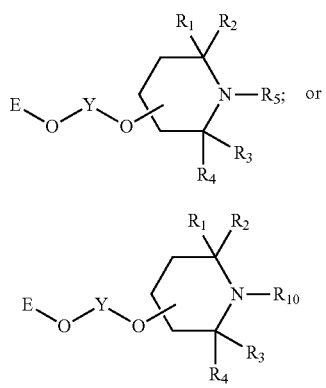

wherein E, Y, $R_1$-$R_5$ and $R_{10}$ are defined herein. Such protected antioxidants have surprising and unexpected advantages over antioxidants and protected antioxidants known in the art. These surprising and unexpected advantages include, but are not limited to, improved stability against complete hydrolysis; reduced free radical scavenging in protected form; enhanced free radical scavenging in de-protected form; enhanced peroxide decomposing ability; the tocopheryl radical or the tocotrienolyl radical, as the terms are defined herein, provides improved compatability with. e.g., polyethylene, due to the presence of a long hydrocarbon "tail," where the long hydrocarbon tail improves performance as an antioxidant by promoting uniform distribution and compatability (e.g., solubility) with the polymer; the tocopheryl radical or the tocotrienolyl radical, as the terms are defined herein, is capable of secondary stabilization after scavenging initial free radical; and the long hydrocarbon tail that is part of the tocopheryl radical or the tocotrienolyl radical, as the terms are defined herein, provides for capability of crosslinking with, e.g., polyethylene, which substantially immobilizes the protected antioxidant and, in some instances, the antioxidant, making the protected antioxidant and/or antioxidant substantially permanent and substantially non-extractable.

In one embodiment, the invention relates to a composition comprising:

ultrahigh molecular weight polyethylene; and at least one compound of the formula (I) or (Ib) (e.g., two compounds of the formula (I), wherein the two compounds of the formula (I) are different):

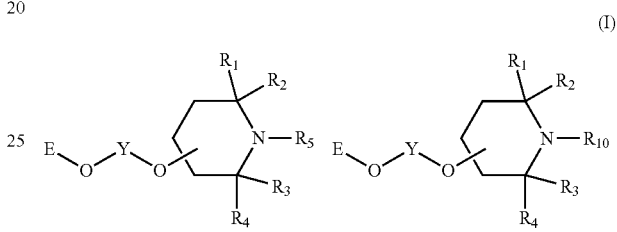

(Ib)or a salt thereof or combinations thereof;

wherein:

$R_1$, $R_2$, $R_3$, $R_4$, and $R_5$ are each, independently, hydrogen or alkyl;

$R_{10}$ is —$OR_{11}$ wherein $R_{11}$ is hydrogen or alkyl, or —O.;

E represents a tocopheryl radical or a tocotrienol radical; and

Y represents the groups:

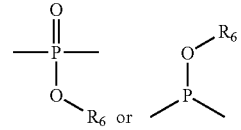

wherein $R_6$ is hydrogen, alkyl, a tocopheryl radical, a tocotrienol radical or a radical of the formula:

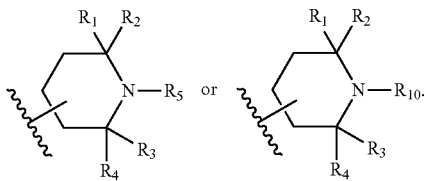

In another embodiment, the invention relates to a method comprising:

combining ultrahigh molecular weight polyethylene and at least one compound of the formula (I) or (Ib) (e.g., two compounds of the formula (I), wherein the two compounds of the formula (I) are different):

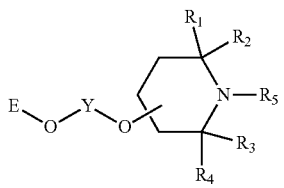
(I)

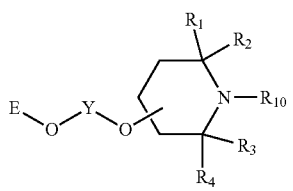
(Ib)

or a salt thereof or combinations thereof;
wherein:
$R_1$, $R_2$, $R_3$, $R_4$, and $R_5$ are each, independently, hydrogen or alkyl;
$R_{10}$ is —$OR_{11}$ wherein $R_{11}$ is hydrogen or alkyl, or —O.;
E represents a tocopheryl radical or a tocotrienol radical; and
Y represents the groups:

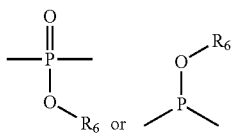

wherein $R_6$ is hydrogen, alkyl, a tocopheryl radical a tocotrienol radical or a radical of the formula:

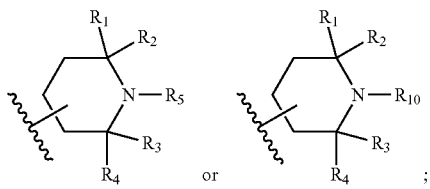

and
irradiating the combined ultrahigh molecular weight polyethylene and the compound of the formula (I) to crosslink the ultrahigh molecular weight polyethylene.

Additional aspects, features, embodiments, and examples are described in more detail below.

DETAILED DESCRIPTION OF THE INVENTION

Certain embodiments described herein include one or more of a protected antioxidant. The phrase "protected antioxidant" refers to a compound of the formula (I) or (Ib):

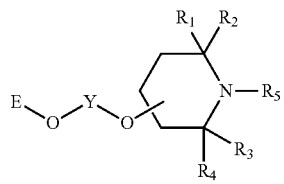
(I)

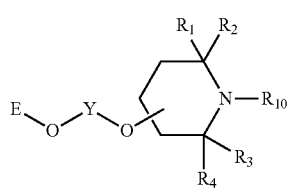
(Ib)

or a salt thereof or combinations thereof;
wherein:
$R_1$, $R_2$, $R_3$, $R_4$, and $R_5$ are each, independently, hydrogen or alkyl;
$R_{10}$ is —$OR_{11}$ wherein $R_{11}$ is hydrogen or alkyl, or —O.;
E represents a tocopheryl radical or a tocotrienolyl radical; and
Y represents the groups:

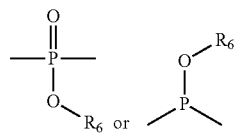

wherein $R_6$ is hydrogen, alkyl, a tocopheryl radical, a tocotrienolyl radical or a radical of the formula:

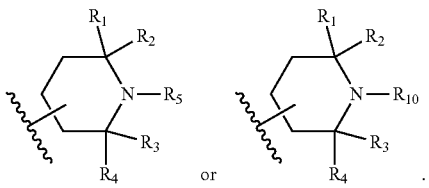

Those of ordinary skill in the art will recognize that when $R_{10}$ represents —O.; that the group N—O represents a nitroxyl radical.

In some embodiments, the compound of the formula (I) is a compound of the formula (Ia):

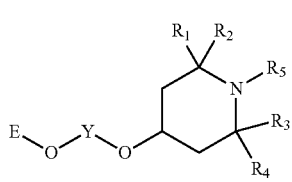
(Ia)

In other embodiments, the compound of the formula (Ib) is a compound of the formula (Ic):

(Ic)

As used herein, the term "tocopheryl radical" broadly refers to a radical of the formula (II):

(II)

wherein $R_7$, $R_8$, and $R_9$ are each independently hydrogen, alkyl or alkenyl. In some embodiments, one or more of the methyl groups on the hydrocarbon chain extending from the benzopyran ring may lie "below the plane of the paper," such that the compound of the formula (II) may be a radical of the formula (IIa):

(IIa)

In some embodiments, in the compounds of the formulae (II) and (IIa), $R_7$, $R_8$, and $R_9$ are each alkyl, preferably methyl (alpha-tocopheryl radical). In some embodiments, $R_7$ and $R_9$ are each alkyl, preferably methyl, and $R_8$ is hydrogen (beta-tocopheryl radical). In some embodiments, $R_8$ and $R_9$ are each alkyl, preferably methyl, and $R_7$ is hydrogen (gamma-tocopheryl radical). In some embodiments, $R_7$ and $R_8$ are each hydrogen and $R_9$ is alkyl, preferably methyl (delta-tocopheryl radical).

As used herein, the term "tocotrienolyl radical" broadly refers to a radical of the formula (III):

(III)

wherein $R_7$, $R_8$, and $R_9$ are each independently hydrogen, alkyl or alkenyl. In some embodiments, the term "tocotrienolyl radical" also broadly refers to a radical of the formula (IIIa):

(IIIa)

In some embodiments, in the compounds of the formulae (III) and (IIa), $R_7$, $R_8$, and $R_9$ are each alkyl, preferably methyl (alpha-tocotrienolyl radical). In some embodiments, $R_7$ and $R_9$ are each alkyl, preferably methyl, and $R_8$ is hydrogen (beta-tocotrienolyl radical). In some embodiments, $R_8$ and $R_9$ are each alkyl, preferably methyl, and $R_7$ is hydrogen (gamma-tocotrienolyl radical). In some embodiments, $R_7$ and $R_8$ are each hydrogen and $R_9$ is alkyl, preferably methyl (delta-tocotrienolyl radical).

As used herein, the term "alkyl" broadly refers to straight chain and branched alkyl groups having from 1 to 40 carbon atoms, 1 to about 20 carbon atoms, 1 to 12 carbon atoms, 1 to 8 carbon atoms or 1 to 4 carbon atoms. Such alkyl groups may be substituted or unsubstituted. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

As used herein, the term "alkenyl" broadly refers to straight and branched chain alkyl groups as defined herein, except that at least one double bond exists between two carbon atoms. Such alkenyl groups may be substituted or unsubstituted. Thus, alkenyl groups have from 2 to 40 carbon atoms, or 2 to about 20 carbon atoms, 2 to 12 carbon atoms, 2 to 8 carbon atoms or 2 to 4 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, hexadienyl, and the like.

As used herein, the term "substituted" broadly refers to a group in which one or more hydrogen atoms contained therein are replaced by one or more "functional groups" or "substituents." Examples of substituents or functional groups include, but are not limited to, halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents include F, Cl, Br, I, OR, OC(O)N(R')$_2$, CN, NO, NO$_2$, ONO$_2$, azido, CF$_3$, OCF$_3$, R', =O (oxo), =S (thiono), C(O), S(O), methylenedioxy, ethylenedioxy, N(R)$_2$, SR, SOR, SO$_2$R', SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or wherein two R groups bonded to a nitrogen atom or to adjacent nitrogen atoms can together with the nitrogen atom or atoms form a heterocyclyl.

As used herein, the term "acyl" broadly refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. Where the carbonyl carbon atom is bonded to a hydrogen, the group is a "formyl" group. Where the carbonyl carbon atom is bonded to a halogen atom, the group is a "haloacyl" group. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms (e.g., nitrogen and oxygen). A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like.

As used herein, the term "cycloalkyl" broadly refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Such cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The cycloalkyl group may have one more unsaturated bonds.

As used herein, the terms "halo" or "halogen" or "halide," by themselves or as part of another substituent, mean, unless otherwise stated, a fluorine, chlorine, bromine, or iodine atom, preferably, fluorine, chlorine, or bromine.

As used herein, the term "cycloalkylalky" broadly refers to alkyl groups as defined herein in which a hydrogen or carbon bond of an alkyl group is replaced with a bond to a cycloalkyl group as defined herein.

As used herein, the term "aryl" broadly refers to cyclic aromatic hydrocarbons that do not contain heteroatoms in the ring. Such aryl groups may be substituted or unsubstituted. Aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative, non-limiting substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

As used herein, the term "aralkyl" broadly refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl group are alkenyl groups as defined herein in which a hydrogen or carbon bond of an alkenyl group is replaced with a bond to an aryl group as defined herein. A representative aralkenyl group is a styryl group.

As used herein, the term "heterocyclyl" broadly refers to aromatic and non-aromatic ring groups containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups, such as cycloalkyl groups. The heterocyclyl group may have one more unsaturated bonds. Representative heterocyclyl groups include, but are not limited to, oxiranyl, aziridinyl, oxetanyl, azetidinyl, furanyl, pyrrolyl, indolyl, imidazolyl, pyrazolyl, indazolyl, tetrazolyl, 2H-pyranyl, pyridinyl, quinolinyl, piperidinyl, pyrazinyl, morpholinyl, oxepinyl, diazepinyl, and the like.

As used herein, the term "heterocyclylalkyl" broadly refers to alkyl groups as defined herein in which a hydrogen or carbon bond of an alkyl group is replaced with a bond to a heterocyclyl group as defined herein.

As used herein, the term "amine" broadly refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions, where the nitrogen contains a positive charge.

As used herein, the term "amino group" broadly refers to a substituent of the form —NH$_2$, —NHR, —NR$_2$, —NR$_3^+$, wherein each R is independently selected, and protonated forms of each, except for —NR$_3^+$, which cannot be protonated; or to the group —N(R)— and protonated forms thereof. Accordingly, any compound substituted with an amino group can be viewed as an amine. An "amino group"

within the meaning herein can be a primary, secondary, tertiary or quaternary amino group, preferably a primary or a secondary amino group.

The protecting group or protecting moieties can be added to prevent, or reduce to at least some degree, the antioxidant from scavenging free radicals when the protected antioxidant is added, for example, to a composition that is exposed to ionizing irradiation to promote crosslinking in the composition. The protective group or protecting moiety comprised in the compounds of the formula (I) is the moiety of the formula (IV) or (IVa):

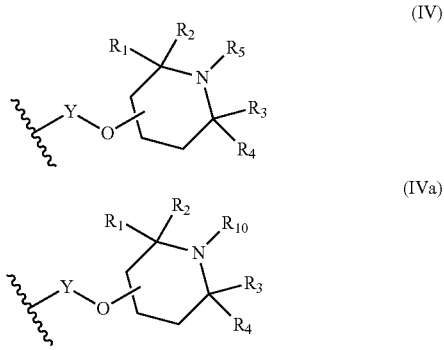

wherein $R_1$-$R_5$, $R_{10}$, and Y are as defined herein.

As used herein, the term "antioxidant" encompasses protected antioxidant, deprotected antioxidant, and unprotected antioxidant.

The term "deprotected antioxidant" broadly refers to an antioxidant wherein at least some portion of the protecting group or protecting moiety of the protected antioxidant is removed from the protected antioxidant. Either all or some portion of the protecting group can be removed to provide a deprotected antioxidant, which may have the same chemical structure as the original antioxidant, prior to protection, or may be some chemically modified form of the antioxidant that is different than either of the antioxidant or the protected antioxidant. Thus, in some embodiments, a "deprotected antioxidant" may be a compound of the formula (V) or (VI):

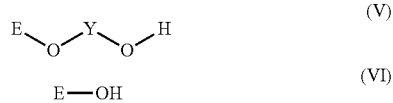

wherein E and Y are as defined herein. Unlike the protected antioxidant, the deprotected antioxidant may be effective to scavenge free radicals.

The term "unprotected antioxidant" refers to an antioxidant that has not been reacted with a protecting group, and, instead, is used in its native form. In instances where the protecting group is entirely removed from a protected antioxidant to provide a fully deprotected antioxidant, the unprotected antioxidant and the deprotected antioxidant can have the same chemical structure. Thus, for example, the unprotected antioxidant may have the same formula as a compound of the formula (VI). In some embodiments, it may be advantageous to have only the protected antioxidant present in the compositions described herein (e.g., UHMWPE compositions). But in some instances, it may be advantageous to have deprotected antioxidant and/or unprotected antioxidant present in the compositions described herein.

In certain examples, the deprotected antioxidants described herein can be used to reduce or prevent oxidation of the accompanying substrate (e.g., UHMWPE). For example, the antioxidant can prevent oxidation of polymer chains in the substrate, which can lead to chain scission and result in reduced molecular weight and/or subsequent embrittlement of the substrate. Oxidation of the substrate can be initiated by the formation of one or more radical species that can be generated thermally, photolytically or by high energy radiation.

In certain examples, a protected antioxidant may be used in combination with an unprotected antioxidant and/or a deprotected antioxidant. For example, a protected antioxidant where E is a tocopheryl radical may be used in combination with a deprotected antioxidant where E is also a tocopheryl radical or a tocotrienolyl radical and/or an unprotected antioxidant where E is a tocopheryl radical or a tocotrienolyl radical. In some embodiments other compounds having antioxidant activity, including flavinoids and carotenoids, may be added to the compositions of the embodiments of the present invention, such that the polymer compositions of the embodiments of the present invention contain two, three, four, five, six or more different compounds having antioxidant activity.

In some embodiments, the protecting group of formula (IV) and (IVa) may be removed by any suitable means, including hydrolysis by treating the polymer compositions comprising the protected antioxidant with water or an aqueous solution or exposing the compositions of the embodiments of the present invention to ambient moisture.

In some embodiments, the protected antioxidant of the embodiments of the present invention may be used in combination with a stabilizer or co-stabilizer. In certain instances, the stabilizer or co-stabilizer can act to stabilize the protected antioxidant itself, whereas in other examples, the stabilizer or co-stabilizer can react more readily with water or other species to prevent degradation of the protected antioxidant. In certain examples, an amine can be used as a stabilizer such that the amine can either react with species that promote degradation of the protected antioxidant or stabilize the protected antioxidant. Suitable stabilizers include, but are not limited to, 2,2,6,6-tetramethylpiperidine, a tertiary amine, and a metallic soap. Such stabilizers can be particularly desired where low irradiation dose levels are used, e.g., sterilization, which typically do not exceed 40 kGy. Such low radiation dose levels can be used to reduce the level of crosslinking In certain embodiments, the protected antioxidants, deprotected antioxidants, and unprotected antioxidants can be added to a polymer to provide an antioxidant effect to that polymer. As discussed in more detail below, the antioxidant can be doped into, diffused into, mixed with, blended with, or combined in other manners to impart some antioxidant effect to the resulting combination. The particular polymer selected for use with the antioxidants can depend, at least in part, on the final desired product or article. Illustrative articles and polymers that can be used to produce them are described in more detail below.

In certain embodiments, the composition of the embodiments of the present invention can include a crosslinkable polymer. The crosslinkable polymer can be any polymer that can be cross-linked using radiation, a chemical crosslinking agent or that can be physically cross-linked under suitable conditions. Those polymers that are crosslinkable using ionization radiation are particularly desirable for use. In some examples, the polymer can be a thermoplastic polymer such as, for example, an acrylonitrile butadiene styrene (ABS) polymer, an acrylic polymer, a celluloid polymer, a cellulose acetate polymer, a cycloolefin copolymer (COC), an ethylene-vinyl acetate (EVA) polymer, an ethylene vinyl alcohol (EVOH) polymer, a fluoroplastic, an ionomer, an acrylic/PVC alloy, a liquid crystal polymer (LCP), a polyacetal polymer (POM or Acetal), a polyacrylate polymer, a polyacrylonitrile polymer (PAN or Acrylonitrile), a polyamide polymer (PA or Nylon), a polyamide-imide polymer (PAI), a polyaryletherketone polymer (PAEK or Ketone), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polyethylene terephthalate polymer (PET), a polycyclohexylene dimethylene terephthalate polymer (PCT), a polycarbonate polymer, a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPO), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), and a styrene-acrylonitrile polymer (SAN). The use of polyethylenes may be particularly desirable where the resulting polymer composition is used to provide an implant or other medical or dental device. Illustrative types of polyethylene include, for example, ultra high molecular weight polyethylene (UHMWPE), ultra low molecular weight polyethylene (ULMWPE), high molecular weight polyethylene (HMWPE), high density polyethylene (HDPE), high density cross-linked polyethylene (HDXLPE), cross-linked polyethylene (PEX or XLPE), medium density polyethylene (MDPE), low density polyethylene (LDPE), linear low density polyethylene (LLDPE) and very low density polyethylene (VLDPE). In some examples, a polypropylene can be used. A polypropylene may be particularly desirable where the final product is a mesh, stent, breast implant material, suture material or other medical device. In one alternative, a polypropylene (or other polymer) may be used as one layer in a multi-layered medical device. Illustrative polypropylenes include, but are not limited to, a homopolymeric polypropylene, a block copolymeric polypropylene, and a random copolymeric polypropylene. In certain examples, the polymers used in the compositions described herein can be copolymerized with one or more monomers or polymers.

In certain examples, the crosslinkable polymer can be ultrahigh molecular weight polyethylene (UHMWPE). UHMWPE is a semi crystalline, linear homopolymer of ethylene, which may be produced by stereospecific polymerization with a Ziegler-Natta catalyst at low pressure (6-8 bar) and low temperature (66-80° C.). The synthesis of nascent UHMWPE results in a fine granular powder. The molecular weight and its distribution can be controlled by process parameters such as temperature, time and pressure. UHMWPE generally has a molecular weight of at least about 2,000,000 g/mol. Suitable UHMWPE materials for use as raw materials may be in the form of a powder or mixture of powders. The UHMWPE material may be prepared almost entirely from UHMWPE powder, or may be formed by combining UHMWPE powder with other suitable polymer materials. In one embodiment, the UHMWPE material may include at least about 50 w/w % UHMWPE. Examples of suitable UHMWPE materials include GUR 1020 and GUR 1050 available from Ticona Engineering Polymers. Suitable polymer materials for use in combination with the UHMWPE materials may include disentangled polyethylene, high pressure crystallized polyethylene and various other "super tough" polyethylene derivatives. In addition, biocompatible non-polyethylene polymers may also be suitable for use in certain embodiments.

In certain examples, the compositions may also include suitable additives that impart a desired physical or chemical property. Illustrative suitable additives include, but are not limited to radiopaque materials, antimicrobial materials such as silver ions, antibiotics, and microparticles and/or nanoparticles serving various functions. Preservatives, colorants and other conventional additives may also be used.

In certain embodiments, the antioxidant and polymer material may be combined via a number of known processes to form a blend. Such processes include physical mixing, mixing with the aid of a solvent, mixing with the aid of a solvent (e.g., $CO_2$) under supercritical temperature and pressure conditions, and ultrasonic mixing. Suitable mixing processes of these types are also described, for example, in U.S. Pat. Nos. 6,448,315 and 6,277,390, the disclosures of which are hereby incorporated by reference.

In one embodiment, the protected antioxidant can be added directly to the polymer material in the absence of any solvent and mixing may occur for a desired period. In other examples, the protected antioxidant can be added to a solvent to suspend or dissolve the protected antioxidant and the resulting fluid can be combined with the polymer. Such a combination may be performed dropwise, incrementally with or without mixing or by combining an entire amount of a selected volume of antioxidant with a selected amount of polymer. In certain examples, protected antioxidant dissolved in, e.g., ethanol, can be added drop-wise to, e.g., a powdered UHMWPE material while mixing. The ethanol may then be removed via a vacuum dryer or similar apparatus.

In certain embodiments, the polymer material and the protected antioxidant may be mixed until a substantially uniform distribution of the antioxidant, e.g., in either protected, deprotected or unprotected forms taken together, is present at least at a surface region of the blend. The term "surface region" refers to a region of a crosslinked polymer blend extending from a surface of the blend to some depth or range of depths below the surface. For example, implants formed from the crosslinked polymer/antioxidant blend may exhibit a substantially uniform distribution of the antioxidant to a surface depth of at least 3 mm, more particularly, at least 5 mm. Other embodiments may exhibit a substantially uniform distribution of antioxidant to a surface depth of at least 10 mm, more particularly at least 15 mm, even more particularly at least 20 mm. In further embodiments, the crosslinked polymer/antioxidant blend may have a substantially uniform distribution of antioxidant throughout the blend. While the antioxidant may be present in a substantially uniform distribution throughout the blend, various areas of the crosslinked polymer may have one form or another of the antioxidant, e.g., protected versus deprotected form. Thus, specific regions or areas of the crosslinked polymer may include only protected antioxidant, deprotected antioxidant or unprotected antioxidant, whereas other areas or regions may include two or more of these forms.

The term "substantially" or "substantial" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more (e.g., 100%).

In certain examples, the surface region may include a combination of protected and deprotected antioxidant, protected and unprotected antioxidant, or protected, deprotected and unprotected antioxidant. For example, it may be desirable to include both protected and deprotected antioxidant as secondary and primary antioxidants, respectively. In addition, as deprotected antioxidant is consumed by reaction with free radicals, more of the protected antioxidant can be converted to deprotected antioxidant for use as a primary antioxidant. In certain examples, a protected antioxidant having more stability, for example to hydrolysis, can be used such that a slow release of deprotected antioxidant would occur with the rate of release corresponding to conditions such as hygroscopic tendencies of the polymer, thickness, moisture availability, and stability of the protected antioxidant. In other examples, a protected antioxidant having less stability, for example to hydrolysis, can be used such that a faster release of deprotected antioxidant would occur. Stability of the antioxidant can be controlled by selecting the particular group or groups present on the antioxidant (e.g., $R_7$, $R_8$, and $R_9$). For example, the rate of hydrolysis of the protecting group may be influenced by increasing or decreasing the steric bulk around the aromatic ring bearing the groups $R_7$, $R_8$, and $R_9$. Generally speaking, the more sterically hindered the aromatic ring, the slower the rate of hydrolysis of the protecting group. And the less sterically hindered the aromatic ring, the faster the rate of hydrolysis of the protecting group.

Where multiple forms (protected, deprotected, and unprotected) of the antioxidant are present, the resulting implant may be treated post-deprotection to add protected or unprotected antioxidant at a desired amount, particularly if the deprotection conditions result in deprotection of substantially all of the protected antioxidant. Alternatively, the deprotection conditions may be selected such that both protected and deprotected antioxidant remain present. In certain instances, the surface region of the implant may include a substantially uniform distribution of deprotected antioxidant, and regions below the surface region may include a substantially uniform distribution of protected antioxidant. As deprotected antioxidant at the surface reacts with free radicals, more of the protected antioxidant can be converted to deprotected antioxidant and can migrate towards the surface of the polymer to provide effective antioxidant protection.

In other examples, the entire implant may include a combination of protected and deprotected antioxidant, protected and unprotected antioxidant, or protected, deprotected and unprotected antioxidant throughout the polymer. Such antioxidants may be uniformly dispersed throughout the polymer. By including different forms of the antioxidant throughout the polymer, the forms may be able to convert between each other such that an effective amount of primary antioxidant, secondary antioxidant or both are present in the implant over the implant's projected lifetime. In this manner, the overall longevity of the implant may increase, which can result in fewer replacement surgeries and failed implants.

In certain embodiments, during preparation of the polymer composition, combination of techniques may be used including mixing, blending, doping, diffusing and the like to provide a desired gradient, distribution or other arrangement of antioxidant within the polymer. For example, the polymer can first be crosslinked, either in the presence of absence of any protected antioxidant, followed by soaking of the crosslinked polymer in protected antioxidant, deprotected antioxidant or unprotected antioxidant. It may be desirable to crosslink the polymer in the presence of protected antioxidant that has been blended with the polymer and then soak the resulting crosslinked polymer in the presence of an unprotected antioxidant. In this manner, a deprotection step may be omitted, and deprotection of the protected antioxidant can occur gradually in the use environment of the crosslinked polymer composition.

In certain embodiments, the combination of the polymer and protected antioxidant can be exposed to crosslinking conditions such that the polymer chains crosslink to a desired degree. Such crosslinking may take various forms including, but not limited to, using radiation, using a chemical crosslinking agent or using conditions to promote physical cross-linking In chemical cross-linking processes, a cross-linking agent such as, for example, dicumyl peroxide is blended with the polymer/protected antioxidant combination and heat is applied to promote the cross-linking reaction. In the radiation cross-linking process, the polymer is irradiated with high energy ionizing radiation, and the resulting transfer of energy to the polymer produces crosslinking between the individual polymer chains. In physical cross-linking processes, the linking may take the form of entanglements, crystallites, or hydrogen-bonded structures. One example of physical crosslinking is exposing the polymer composition to freezing and thawing.

In certain other embodiments, the combination of the polymer, protected antioxidant, and cross-linking-agent can be exposed to conditions that effect a substantial amount of consolidation, but not a substantial amount of cross-linking For example, the combination of the polymer, protected antioxidant, and cross-linking-agent can be heated to a temperature where there is substantial consolidation (e.g., at least about 50%, 60%, 70%, 80%, 90%, 95%, 96%, 97%, 98%, 99%, 99.5%, 99.9%, 99.99%, or at least about 99.999% or more, including 100%, consolidation), but there is not a substantial amount of cross-linking In some embodiments, the temperature where there is substantial consolidation, but there is not a substantial amount of cross-linking, can be a temperature from about 180° C. to about 220° C. (e.g., from about 180° C. to about 200° C., from about 180° C. to about 195° C., and about 180° C. to about 190° C.). In some embodiments, the temperature where there is substantial consolidation, but there is not a substantial amount of cross-linking can be a temperature from about 180° C. to about 220° C. (e.g., from about 180° C. to about 200° C., from about 180° C. to about 195° C., and about 180° C. to about 190° C.), where the cross-linking agent has a half-life ($t_{1/2}$) of about 1 hour. Cross-linking agents having a $t_{1/2}$ of about 1 hour include, but are not limited to, peroxides such as hydroperoxides including, but not limited to, t-butyl hydroperoxide ($t_{1/2}$ is about 1 hour at 185° C.; available from Akzo Nobel as TRIGONOX® A-80 and TRIGONOX® A-W70) and t-amyl hydroperoxide ($t_{1/2}$ is about 1 hour at 190° C.; available from Akzo Nobel as TRIGONOX® TAHP-W85).

The term "not a substantial amount of cross-linking" as used herein refers to less than about 90%, 80%, 70%, 60%, 50%, 40%, 30%, 20%, 10%, 5%, 3%, 1%, 0.5%, 0.1%, 0.01%, or less than about 0.001% or less (e.g., 0%) crosslinking.

In examples where radiation crosslinking is used, the radiation used may be visible light radiation, infrared radiation, ultraviolet radiation, electron beam radiation, gamma radiation, or X-ray radiation. Where ionizing radiation is employed to effect the cross-linking reaction, the radiation can be obtained from any suitable source such as an atomic pile, a resonant transformer accelerator, a Van de Graaff electron accelerator, a Linac electron accelerator, a betatron, a synchrotron, a cyclotron, or the like. Radiation from these sources will produce ionizing radiation such as electrons, protons, neutrons, deuterons, gamma rays, X rays, alpha particles, and beta particles. Where ionizing radiation is used, a sufficient radiation dose rate and/or absorbed dose can be used to induce crosslinking and/or control the degree of crosslinking.

In certain examples, the use of electron beam radiation may be particularly desirable to provide an implant having desired physical properties. Electron beam radiation exposure may be performed using conventionally available electron beam accelerators. One commercial source for such an accelerator is IBA Technologies Group, Belgium. Suitable accelerators may produce an electron beam energy between about 2 and about 50 MeV, more particularly about 10 MeV, and are generally capable of accomplishing a selected radiation dose and/or dosage rate. Electron beam exposure may be carried out in a generally inert atmosphere, including for example, an argon, nitrogen, vacuum, or oxygen scavenger atmosphere. Exposure may also be carried out in air under ambient conditions.

In certain examples, crosslinking may also be performed in the presence of an additive that can promote or deter crosslinking, depending on the desired level of crosslinking in the final polymer. Illustrative crosslinking promoters include, but are not limited to, trimethylolpropane triacrylate, trimethylolpropane trimethacrylate, pentaerythritol tetraacrylate, and pentaerythritol tetramethacrylate. In certain instances, unprotected antioxidant or deprotected antioxidant can be present to reduce the degree of crosslinking Alternatively, other reagents that can scavenge free radicals can be present to reduce the degree of crosslinking in the polymer composition.

In certain examples, crosslinking can take place in an organic solvent to prevent premature deprotection of the protected antioxidant. The resulting cross-linked polymeric composition can then be exposed to an aqueous solution to deprotect at least some of the protected antioxidant or post-crosslinking processing such as, for example, soaking, dipping, molding, annealing, etc., may be performed as desired.

In certain examples, prior to and/or after crosslinking, the polymer/antioxidant composition may be subjected to one or more temperature treatments. In one embodiment, the composition may be heated above room temperature, more particularly above about 100° C., even more particularly between about 120° C. and 130° C. Where heat treatment occurs, the heat treatment can be below, at or above the melt temperature of the polymer. In certain embodiments, it may be desirable to heat treat the polymer/antioxidant composition below the melt temperature. In other examples, the polymer composition can remain at room temperature or be cooled below room temperature, for example, below the glass transition temperature of the polymer composition.

In certain embodiments, after irradiation the polymer composition can be annealed by exposure to heat. Alternatively or additionally, the crosslinked polymer composition can be subjected to the mechanical annealing processes reported in U.S. Pat. No. 6,853,772, which is hereby incorporated by reference. In one embodiment, however, no pre- or post-irradiation temperature and/or annealing treatments are performed.

In certain examples, one or more agents, e.g., bioactive agents, can be added to the polymer composition. Such addition can be accomplished during any stage of preparation but may be desirable after any heat treatments are performed to reduce the likelihood of deactivation of the bioactive agent. Illustrative agents include, but are not limited to, an antibiotic, a steroid, a drug, a growth factor such as bone morphogenic protein, an osteocyte, an osteoclast or other cells, a vitamin, a chondroitin, a glucosamine, a glycosoaminglycan, high energy phosphates such as phosphoenolpyruvate, ATP, 5'-AMP and other small molecule biologics or other chemical or biological agents. In some examples, the polymer composition may be loaded with stem cells, and the polymer composition can act as a scaffold to permit growth and differentiation of bone or cartilage within the polymer framework. The presence of a protected/deprotected antioxidant in the polymer composition can act to prevent degradation of the scaffold in its use environment and may also provide some oxidative protection to the bioactive agent or stem cells loaded into the scaffold.

In certain examples, subsequent to or after production of the crosslinked polymer composition, the composition may be molded, compressed, consolidated or otherwise processed to provide a desired shape, part size or other physical attributes to render the part suitable for its intended use. Such processing may take place in a low humidity and low oxygen environment to prevent premature oxidation of the part. In some instances, processing can be combined with exposure to high humidity levels to promote deprotection of the protected antioxidant.

In certain embodiments, additional components may be combined with the polymer composition at any time during the process. In one embodiment, tribological components such as metal and/or ceramic articulating components and/or preassembled bipolar components may be joined with the polymer composition. In other embodiments, metal backing (e.g., plates or shields) may be added. In further embodiments, surface components such a trabecular metal, fiber metal, Sulmesh™ coating, meshes, cancellous titanium, and/or metal or polymer coatings may be added to or joined with the polymer composition. Still further, radiomarkers or radiopacifiers such as tantalum, steel and/or titanium balls, wires, bolts or pegs may be added. Further yet, locking features such as rings, bolts, pegs, snaps and/or cements/adhesives may be added. These additional components may be used to form sandwich implant designs, radiomarked implants, metal-backed implants to prevent direct bone contact, functional growth surfaces, and/or implants with locking features. Additional suitable components for combining with the polymer compositions described herein to provide an implant having a desired physical structure and/or desired physical features will be readily selected by the person of ordinary skill in the art, given the benefit of this disclosure.

In certain embodiments, the compositions described herein include a pre-crosslinked polymer, e.g., UHMWPE, and a protected antioxidant. In some examples, the protected antioxidant is uniformly dispersed throughout the pre-crosslinked polymer to provide a blend of pre-crosslinked polymer and protected antioxidant. In certain instances, the polymer may be crosslinked in the presence of the protected antioxidant. As described herein, deprotection can be accomplished post-crosslinking to provide a deprotected antioxidant within the crosslinked polymer. In certain instances, deprotection can provide a mixture of deprotected antioxidant and protected antioxidant. In some examples, the protected antioxidant and the deprotected antioxidant can be present in the polymer composition at a ratio of about 20:1, 15:1, 10:1, 5:1, 4:1, 3:1, 2:1, 1:1, 1:2, 1:3, 1:4, or 1:5. In certain instances, the polymer composition may also include an unprotected antioxidant.

In certain embodiments, the compositions described herein include pre-crosslinked polymer, e.g., UHMWPE, and an antioxidant mixture comprising a protected antioxidant and an unprotected antioxidant. In some examples, the antioxidant mixture is dispersed throughout the pre-crosslinked polymer to provide a blend of pre-crosslinked polymer and antioxidant mixture. In certain instances, the polymer may be crosslinked in the presence of the protected antioxidant and the unprotected antioxidant. As described herein, deprotection can be accomplished post-crosslinking to provide a deprotected antioxidant within the crosslinked polymer. In certain instances, deprotection can provide a mixture of deprotected antioxidant, protected antioxidant and unprotected antioxidant. In some examples, the protected antioxidant and the unprotected antioxidant can be present in the polymer composition at a ratio of about 5:1, 4:1, 3:1, 2:1, 1:1, 1:2, 1:3, 1:4, or 1:5.

In certain examples, the polymer compositions described herein can include a blend of a polymer, e.g., UHMWPE, and an antioxidant mixture comprising a protected antioxidant and a deprotected antioxidant, the blend comprising a substantially uniform distribution of the antioxidant mixture in the polymer. In some examples, the protected antioxidant and the deprotected antioxidant can be present in the polymer composition at a ratio of about 5:1, 4:1, 3:1, 2:1, 1:1, 1:2, 1:3, 1:4, or 1:5. In some embodiments, the antioxidant mixture further comprises an unprotected antioxidant.

In certain embodiments, the polymer compositions described herein can include a blend of a polymer, e.g., UHMWPE, and an antioxidant mixture comprising a protected antioxidant and an unprotected antioxidant, the blend comprising a substantially uniform distribution of the antioxidant mixture in the polymer. In some examples, the protected antioxidant and the unprotected antioxidant can be present in the polymer composition at a ratio of about 5:1, 4:1, 3:1, 2:1, 1:1, 1:2, 1:3, 1:4, or 1:5. In certain embodiments, the antioxidant mixture may further comprise deprotected antioxidant.

In certain examples, a method of making a polymer composition can include mixing a polymer, e.g., UHMWPE, and a protected antioxidant, and exposing the mixed polymer and protected antioxidant to radiation to crosslink the polymer. In certain embodiments, the method can include converting at least some of the protected antioxidant to a deprotected antioxidant. In other embodiments, the method can include, prior to the exposing step, mixing the polymer and the protected antioxidant to provide a blend comprising a substantially uniform distribution of the protected antioxidant throughout the polymer. In certain embodiments, the exposing step comprises exposing the mixed polymer and protected antioxidant to gamma radiation. In other embodiments, the exposing step comprises exposing the mixed polymer and protected antioxidant to electron beam radiation. In additional embodiments, the method can include mixing a deprotected antioxidant with the polymer and the protected antioxidant. In certain instances, the antioxidant of the protected antioxidant and the antioxidant of the deprotected antioxidant are the same base antioxidant. In certain examples, the protected antioxidant and the deprotected antioxidant are present in a ratio of about 5:1, 4:1, 3:1, 2:1, 1:1, 1:2, 1:3, 1:4, or 1:5. In certain embodiments, the method can also include consolidating, prior to the exposing step, the mixed polymer and protected antioxidant. In other embodiments, the exposing step may be performed prior to consolidation and the consolidation may occur after the exposing step.

In certain embodiments, a method of preparing a polymer composition can include doping a protected antioxidant into a polymer, e.g., UHMWPE, to provide a gradient of the protected antioxidant in the polymer. In some examples, the method can include crosslinking the polymer prior to doping with the protected antioxidant. In certain embodiments, the method can include crosslinking the polymer in the presence of the protected antioxidant and then doping the crosslinked polymer with the protected antioxidant to provide the gradient of protected antioxidant. In other embodiments, the method can include doping the polymer with an unprotected antioxidant.

In certain examples, a method of preparing a polymer composition can include mixing a polymer, e.g., UHMWPE, and an antioxidant mixture comprising a protected antioxidant and an unprotected antioxidant, and exposing the mixed polymer and antioxidant mixture to radiation to crosslink the polymer. In some embodiments, the method can include converting at least some of the protected antioxidant to a deprotected antioxidant. In additional embodiments, the method can include mixing the polymer and the antioxidant mixture to provide a blend comprising a substantially uniform distribution of the antioxidant mixture throughout the polymer. In other examples, the method can include exposing the mixed polymer and antioxidant mixture to gamma radiation to crosslink the polymer. In certain examples, the method can include exposing the mixed polymer and antioxidant mixture to electron beam radiation to crosslink the polymer. In certain examples, the method can include mixing a deprotected antioxidant with the polymer. In some examples, the antioxidant of the protected antioxidant and the antioxidant of the deprotected antioxidant comprise the same base antioxidant. In certain examples, the protected antioxidant and the deprotected antioxidant are present in a ratio of about 5:1, 4:1, 3:1, 2:1, 1:1, 1:2, 1:3, 1:4, or 1:5. In certain embodiments, the method can also include consolidating, prior to the exposing step, the mixed polymer and antioxidant mixture. In other embodiments, the exposing step may be performed prior to consolidation and the consolidation may occur after the exposing step.

In certain embodiments, a method of preparing a polymer composition can include mixing a polymer, e.g., UHMWPE, and an antioxidant mixture comprising a protected antioxidant and a deprotected antioxidant, and exposing the mixed polymer and antioxidant mixture to radiation to crosslink the polymer. In certain examples, the method can include converting at least some of the protected antioxidant to deprotected antioxidant after the exposing step. In additional examples, the method can include mixing the polymer, and the antioxidant mixture to provide a blend comprising a substantially uniform distribution of the antioxidant mixture throughout the polymer. In other examples, the exposing step comprises exposing the polymer and the antioxidant mixture to gamma radiation. In certain examples, the exposing step comprises exposing the polymer and the antioxidant mixture to electron beam radiation. In some examples, the method comprises mixing an unprotected antioxidant with the polymer. In certain examples, the antioxidant of the protected antioxidant and the antioxidant of the unprotected antioxidant comprise the same base antioxidant. In additional examples, the protected antioxidant and the unprotected antioxidant are present in a ratio of about 5:1, 4:1, 3:1, 2:1, 1:1, 1:2, 1:3, 1:4, or 1:5. In some examples, the method can include consolidating, prior to the exposing step, the mixed polymer and antioxidant mixture. In certain examples, the method can include converting at least some of the protected antioxidant to deprotected antioxidant after the exposing step. In additional examples, the method can include consolidating the mixed polymer and antioxidant mixture after the exposing step.

In certain embodiments, a method of facilitating production of an implant includes providing a polymer, e.g., UHMWPE, and providing a protected antioxidant. In some examples, the method includes providing instructions for mixing the polymer and the protected antioxidant to provide a substantially uniform distribution of the protected antioxidant in the polymer. In other examples, the method includes providing instructions for exposing the polymer and the protected antioxidant to radiation to crosslink the polymer. In additional examples, the method includes providing instructions to convert at least some of the protected antioxidant to a deprotected antioxidant. In other embodiments, the method includes providing a deprotected antioxidant. In some examples, the method includes providing instructions for doping the protected antioxidant in the polymer, and providing instructions for exposing the polymer comprising the doped protected antioxidant to radiation to crosslink the polymer. In certain examples, the method includes providing instructions for consolidating the mixed polymer and the protected antioxidant, providing instructions for exposing the polymer and the protected antioxidant to radiation to crosslink the consolidated polymer, and providing instructions for converting at least some of the protected antioxidant to a deprotected antioxidant.

In certain embodiments, a method of facilitating production of an implant includes providing a polymer, e.g., UHMWPE, providing a protecting agent, and providing instructions for using the protecting agent to provide a protected antioxidant for use with the polymer. In certain examples, the method can include providing the antioxidant. In some examples, the method can include providing instructions for mixing the polymer and the protected antioxidant to provide a substantially uniform distribution of the protected antioxidant in the polymer. In certain embodiments, the method can include providing instructions for exposing the polymer and the protected antioxidant to radiation to crosslink the polymer, and providing instructions to convert at least some of the protected antioxidant to a deprotected antioxidant. In other examples, the method can include providing a deprotected antioxidant. In some embodiments, the method can include providing instructions for doping the protected antioxidant in the polymer, and providing instructions for exposing the polymer comprising the doped protected antioxidant to radiation to crosslink the polymer. In certain embodiments, the method can include providing instructions for consolidating the mixed polymer and the protected antioxidant, providing instructions for exposing the consolidated polymer and the protected antioxidant to radiation to crosslink the consolidated polymer, and providing instructions for converting at least some of the protected antioxidant to a deprotected antioxidant.

In certain embodiments, a method can include combining ultrahigh molecular weight polyethylene and a protected antioxidant to provide a blend, consolidating the blend of ultrahigh molecular weight polyethylene and a protected antioxidant, and exposing the consolidated blend of ultrahigh molecular weight polyethylene and a protected antioxidant to radiation to crosslink the ultrahigh molecular weight polyethylene. In some examples, the method can include converting at least some of the protected antioxidant to deprotected antioxidant.

In other embodiments, a method can include combining ultrahigh molecular weight polyethylene and a protected antioxidant to provide a blend, exposing the blend of ultrahigh molecular weight polyethylene and a protected antioxidant to radiation to crosslink the ultrahigh molecular weight polyethylene, and consolidating the crosslinked blend of ultrahigh molecular weight polyethylene and a protected antioxidant. In some examples, the method can include converting at least some of the protected antioxidant to deprotected antioxidant.

In certain examples, a method of preparing a polymer composition can include reacting a compound of the formula E-OH with $PCl_3$, to provide a compound of the formula (VII):

(VII)

The compound for the formula (VII) is then reacted with a compound of the formula (VIII) or (VIIIb):

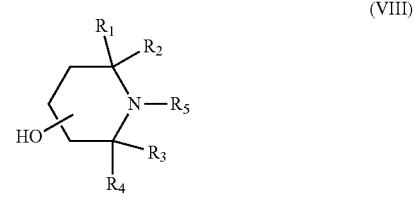

(VIII)

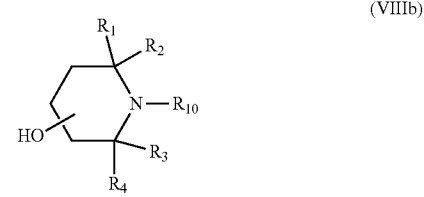

(VIIIb)

to give a compound of the formula (I) or (Ib) (i.e., a protected antioxidant), respectively. The method also includes combining the protected antioxidant with a polymer, e.g., UHMWPE, solidifying the combined polymer and protected antioxidant, and crosslinking the solidified polymer and protected antioxidant. In some examples, the method can include converting at least some of the protected antioxidant to deprotected antioxidant. In other examples, the method can include adding an unprotected antioxidant to the polymer, either before or after solidifying or crosslinking.

In the various examples described herein, the compound of formula (VIII) may be a compound of the formula (VIIIa):

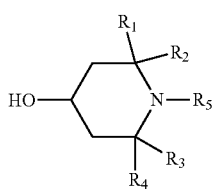

(VIIIa)

and the compound of formula (VIIIb) may be a compound of the formula (VIIIc):

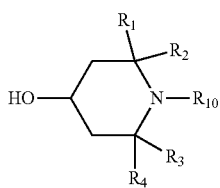

(VIIIc)

In certain examples, a method of preparing a polymer composition can include reacting a compound of the formula E-OH with $PCl_3$, to provide a compound of the formula (VII):

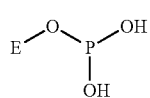

(VII)

The compound for the formula (VII) is then reacted with a compound of the formula (VIII) or (VIIIb):

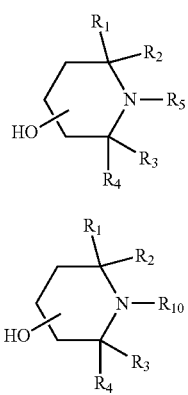

(VIII)

(VIIIb)

to give a compound of the formula (I) or (Ib) (i.e., a protected antioxidant), respectively. The method also includes combining the protected antioxidant with a polymer, e.g., UHMWPE, crosslinking the solidified polymer and protected antioxidant, and solidifying the crosslinked polymer and protected antioxidant. In some examples, the method can include converting at least some of the protected antioxidant to deprotected antioxidant. In other examples, the method can include adding an unprotected antioxidant to the polymer, either before or after crosslinking or solidifying.

In certain examples, a method of producing an implant can include combining a protected antioxidant, e.g., a compound of the formula (I) or (Ib) (or combinations thereof), with a polymer, e.g., UHMWPE, solidifying the combined polymer and protected antioxidant, crosslinking the solidified polymer and protected antioxidant, and forming an implant from the crosslinked polymer and protected antioxidant. In some examples, the method can include converting at least some of the protected antioxidant in the implant to deprotected antioxidant. In other examples, the method can include adding an unprotected antioxidant to the polymer, either before or after solidifying or crosslinking or implant formation.

In certain examples, a method of producing an implant can include combining a protected antioxidant, e.g., a compound of the formula (I) or (Ib) (or combinations thereof), with a polymer, e.g., UHMWPE, crosslinking the solidified polymer and protected antioxidant, and forming the implant from the solidified and crosslinked polymer and protected antioxidant. In some examples, the method can include converting at least some of the protected antioxidant in the implant to deprotected antioxidant. In other examples, the method can include adding an unprotected antioxidant to the polymer, either before or after crosslinking or solidifying or implant formation.

In certain examples, a composition or article may be produced by combining a polymer, e.g., UHMWPE, and a protected antioxidant, e.g., a compound of the formula (I) or (Ib) (or combinations thereof), and exposing the polymer and protected antioxidant to radiation to crosslink the polymer. In certain embodiments, the composition may be produced by converting at least some of the protected antioxidant to a deprotected antioxidant.

In certain embodiments, an article may include a pre-crosslinked polymer, e.g., pre-crosslinked UHMWPE, and a protected antioxidant, e.g., a compound of the formula (I) or (Ib) (or combinations thereof). In some embodiments, an article may include a partially crosslinked polymer, e.g., partially crosslinked UHMWPE, and a protected antioxidant. In other embodiments, an article may include a crosslinked polymer, e.g., crosslinked UHMWPE, and a protected antioxidant. In certain examples, the protected antioxidant is present in a substantially uniform distribution in the pre-crosslinked, partially crosslinked or crosslinked polymer. In other examples, the article can include an unprotected antioxidant. In additional examples, the article can include deprotected antioxidant. In yet other examples, the article can include an additional component joined to the article to form an implant. In some examples, the article comprises at least portions of an artificial hip, hip liner, knee, knee liner, disk replacement, shoulder, elbow, foot, ankle, finger, mandible or bearings in artificial heart.

The technology described herein can provide certain advantages, depending on the exact configuration of the polymer compositions including, for example, improved oxidation stability of the polymer, lower color formation, permits the use of lower radiation levels for an equivalent level of crosslinking, is capable of stabilizing hydroperoxide species as well as free radical species, and permits higher loading rates of antioxidant with less inhibition of crosslinking, which can provide better long term oxidative stability. Thus, it may be possible to crosslink the polymer compositions disclosed herein using radiation doses commonly used for sterilization, e.g., 25-40 kGy, rather than the higher doses typically used in crosslinking processes, e.g., 50-200 kGy.

EXAMPLES

Certain specific examples are described in more detail below to illustrate further some of the aspects and features of the technology described herein.

The present invention can be better understood by reference to the following examples which are offered by way of illustration. The present invention is not limited to the examples given herein.

Example 1

This example describes the synthesis of a compound of the formula:

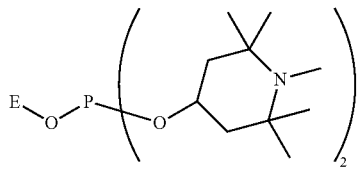

wherein E represents the racemic d,l-alpha tocopheryl radical.

The solvent, $CH_2Cl_2$, and triethylamine (TEA) were dried over type 3A, 8-12 mesh activated molecular sieves. Racemic d,l-alpha tocopherol (VE; $1.146 \times 10^{-2}$ moles) was charged into a dry three-neck Schlenk reaction flask equipped with magnetic stir bar and a dry $N_2$ purge inlet. The flask was then charged with 5 mL dry $CH_2Cl_2$ under dry $N_2$ purge. To the flask was added 5 mL dry TEA (approximately $3.5 \times 10^{-2}$ moles) under dry $N_2$ purge. A solution of $PCl_3$ (1.00 mL; $1.146 \times 10^{-2}$ moles; 10 mL dry $CH_2Cl_2$) was added drop-wise under dry $N_2$ purge to the VE-TEA mixture with stirring. The vessel containing the $PCl_3$ solution was washed with three 5 mL aliquots of dry $CH_2Cl_2$. To this solution was added, in a drop-wise fashion, a solution/dispersion of 1,2,2,6,6-pentamethyl-4-piperidinol ($2.292 \times 10^{-2}$ moles) in 10 mL dry $CH_2Cl_2$ with stirring under dry $N_2$ purge. The vessel containing the piperidinol solution/suspension was washed with three 5 mL aliquots of dry $CH_2Cl_2$.

After one hour, the reaction temperature was raised slowly to 40° C. under dry $N_2$ purge. At that point the Schlenk flask was already equipped with a reflux condenser. The reaction temperature was maintained at 40° C. for one hour. The reaction was allowed to cool to room temperature (about 25° C.). A precipitate had formed. The reaction was then filtered under dry $N_2$ purge. The filtrate was collected in a round-bottomed flask equipped with a condenser and a collection flask and kept under dry $N_2$ purge. The round-bottomed flask was slowly heated to 95° C. to remove volatiles, under dry $N_2$ purge. The product that remained in the round-bottomed flaks was purified by hot filtration under dry $N_2$ purge.

Example 2

This example describes the synthesis of a compound of the formula:

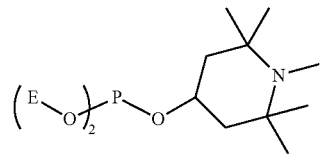

wherein E represents the racemic d,l-alpha tocopheryl radical.

The solvent, $CH_2Cl_2$, and triethylamine (TEA) were dried over type 3A, 8-12 mesh activated molecular sieves. Racemic d,l-alpha tocopherol (VE; $2.292 \times 10^{-2}$ moles) was charged into a dry three-neck Schlenk reaction flask equipped with magnetic stir bar and a dry $N_2$ purge inlet. The flask was then charged with 10 mL dry $CH_2Cl_2$ under dry $N_2$ purge. To the flask was added 5 mL dry TEA (approximately $3.5 \times 10^{-2}$ moles) under dry $N_2$ purge. A solution of $PCl_3$ (1.00 mL; $1.146 \times 10^{-2}$ moles; 10 mL dry $CH_2Cl_2$) was added drop-wise under dry $N_2$ purge to the VE-TEA mixture with stirring. The vessel containing the $PCl_3$ solution was washed with three 5 mL aliquots of dry $CH_2Cl_2$. To this solution was added, in a drop-wise fashion, a solution/dispersion of 1,2,2,6,6-pentamethyl-4-piperidinol ($2.292 \times 10^{-2}$ moles) in 5 mL dry $CH_2Cl_2$ with stirring under dry $N_2$ purge. The vessel containing the piperidinol solution/suspension was washed with three 5 mL aliquots of dry $CH_2Cl_2$.

After one hour, the reaction temperature was raised slowly to 40° C. under dry $N_2$ purge. At that point the Schlenk flask was already equipped with a reflux condenser. The reaction temperature was maintained at 40° C. for one hour. The reaction was allowed to cool to room temperature (about 25° C.). A precipitate had formed. The reaction was then filtered under dry $N_2$ purge. The filtrate was collected in a round-bottomed flask equipped with a condenser and a collection flask and kept under dry $N_2$ purge. The round-bottomed flask was slowly heated to 95° C. to remove volatiles, under dry $N_2$ purge. The product that remained in the round-bottomed flaks was purified by hot filtration under dry $N_2$ purge.

The present invention provides for the following exemplary embodiments, the numbering of which is not to be construed as designating levels of importance:

Embodiment 1 relates to a composition comprising:
ultrahigh molecular weight polyethylene; and
at least one compound of the formula (I) or (Ib):

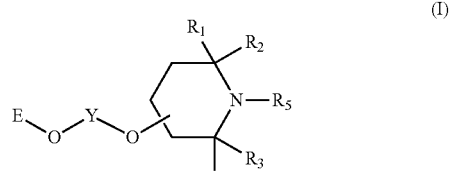

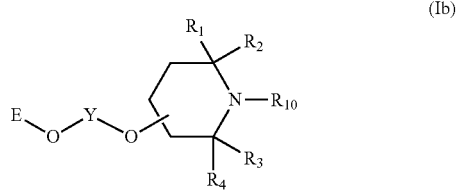

or a salt thereof or combinations thereof;

wherein:

$R_1$, $R_2$, $R_3$, $R_4$, and $R_5$ are each, independently, hydrogen or alkyl;

$R_{10}$ is $-OR_{11}$ wherein $R_{11}$ is hydrogen or alkyl, or $-O\cdot$;

E represents a tocopheryl radical or a tocotrienol radical; and

Y represents the groups:

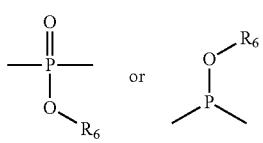

wherein $R_6$ is hydrogen, alkyl, a tocopheryl radical, a tocotrienol radical or a radical of the formula:

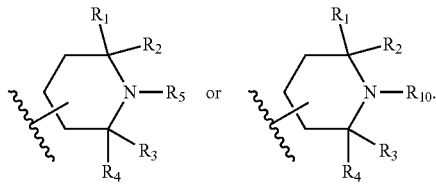

Embodiment 2 relates to the composition of Embodiment 1, wherein the one or more compounds of the formula (I) are substantially uniformly distributed throughout the ultrahigh molecular weight polyethylene.

Embodiment 3 relates to the composition of Embodiments 1-2, wherein E is a tocopheryl radical.

Embodiment 4 relates to the composition of Embodiments 1-3, wherein E is an α-tocopheryl radical.

Embodiment 5 relates to the composition of Embodiments 1-4 wherein $R_6$ is a tocopheryl radical.

Embodiment 6 relates to the composition of Embodiments 1-4, wherein $R_6$ is a radical of the formula:

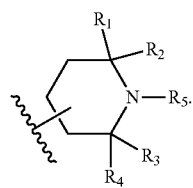

Embodiment 7 relates to the composition of Embodiments 1-4, wherein $R_6$ is a radical of the formula:

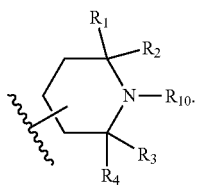

Embodiment 8 relates to the composition of Embodiments 1-7, wherein $R_1$, $R_2$, $R_3$, and $R_4$ are each, independently, alkyl.

Embodiment 9 relates to the composition of Embodiment 8, wherein each alkyl is methyl.

Embodiment 10 relates to the composition of Embodiments 1-6, 8 or 9, wherein $R_5$ is alkyl.

Embodiment 11 relates to the composition of Embodiment 1-6, 8 or 9, wherein $R_5$ is methyl.

Embodiment 12 relates to the composition of Embodiments 1-11, wherein Y represents the group:

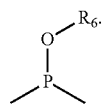

Embodiment 13 relates to the composition of Embodiments 1-12, wherein the compound of formula (I) has the formula (Ia):

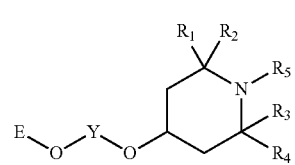

(Ia)

Embodiment 14 relates to the composition of Embodiments 1-12, wherein the compound of formula (Ib) has the formula (Ic):

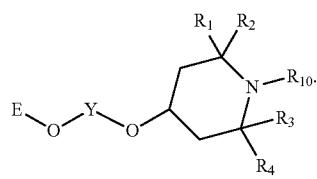

(Ic)

Embodiment 15 relates to the composition of Embodiments 1-14, wherein the ultrahigh molecular weight polyethylene is crosslinked.

Embodiment 16 relates to the composition of Embodiment 1, further comprising a cross-linking agent.

Embodiment 17 relates to the composition of Embodiment 16, wherein the cross-linking agent is a peroxide.

Embodiment 18 relates to the composition of Embodiment 16, wherein the cross-linking agent is a peroxide having a half-life ($t_{1/2}$) of about 1 hour at a temperature from about 180° C. to about 220° C.

Embodiment 19 relates to the composition of Embodiment 16, wherein the cross-linking agent is a hydroperoxide.

Embodiment 20 relates to an orthopedic implant comprising the composition of Embodiments 1-19.

Embodiment 21 relates to a method comprising:
combining ultrahigh molecular weight polyethylene and at least one compound of the formula (I) or (Ib):

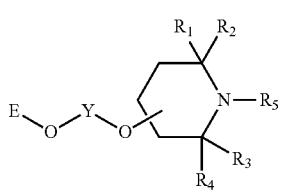

(I)

-continued

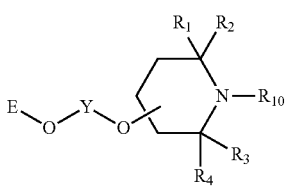
(Ib)

or a salt thereof or combinations thereof;
wherein:
R$_1$, R$_2$, R$_3$, R$_4$, and R$_5$ are each, independently, hydrogen or alkyl;
R$_{10}$ is —OR$_{11}$ wherein R$_{11}$ is hydrogen or alkyl, or —O.;
E represents a tocopheryl radical or a tocotrienol radical; and
Y represents the groups:

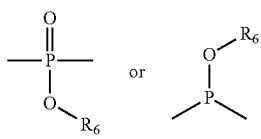

wherein R$_6$ is hydrogen, alkyl, a tocopheryl radical a tocotrienol radical or a radical of the formula:

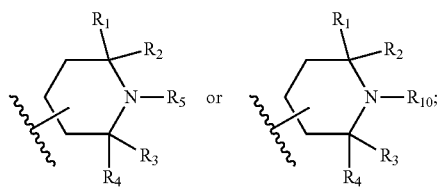

and
irradiating the combined ultrahigh molecular weight polyethylene and the compound of the formula (I) to crosslink the ultrahigh molecular weight polyethylene.

Embodiment 22 relates to the method of Embodiment 21, further comprising converting at least some of the compound of the formula (I) to a compound of the formula EOH, wherein E represents a tocopheryl radical or a tocotrienol radical, after the irradiating step.

Embodiment 23 relates to the method of Embodiments 21-22, further comprising combining the ultrahigh molecular weight polyethylene and the compound of formula (I) to provide a composition wherein the compound of formula (I) is substantially uniformly distributed throughout the ultrahigh molecular weight polyethylene.

Embodiment 24 relates to the method of Embodiments 21-23, wherein the irradiating comprises irradiating with gamma radiation or electron beam radiation.

Embodiment 25 relates to the method of Embodiments 21-24, further comprising solidifying the combined ultrahigh molecular weight polyethylene and compound of the formula (I) prior to the irradiating step.

Embodiment 26 relates to the method of Embodiments 21-24, further comprising solidifying the combined ultrahigh molecular weight polyethylene and compound of the formula (I) after the irradiating step.

Embodiment 27 relates to a method comprising:
combining ultrahigh molecular weight polyethylene, at least one compound of the formula (I) or (Ib):

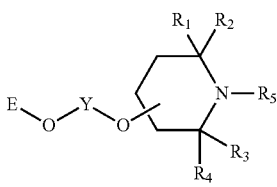
(I)

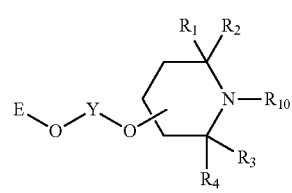
(Ib)

or a salt thereof or combinations thereof;
wherein:
R$_1$, R$_2$, R$_3$, R$_4$, and R$_5$ are each, independently, hydrogen or alkyl;
R$_{10}$ is —OR$_{11}$ wherein R$_{11}$ is hydrogen or alkyl, or —O.;
E represents a tocopheryl radical or a tocotrienol radical; and
Y represents the groups:

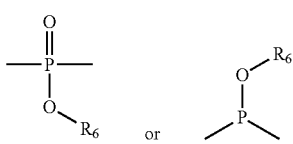

wherein R$_6$ is hydrogen, alkyl, a tocopheryl radical a tocotrienol radical or a radical of the formula:

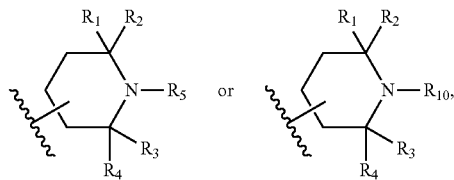

and
a cross-linking agent;
heating the combined ultrahigh molecular weight polyethylene, compound of the formula (I), and cross-linking agent to a temperature where there is substantial consolidation of the ultrahigh molecular weight polyethylenene, but there is not a substantial amount of cross-linking of the ultrahigh molecular weight polyethylene.

What is claimed is:

1. A composition comprising:
ultrahigh molecular weight polyethylene; and
at least one compound of the formula (I) or (Ib):

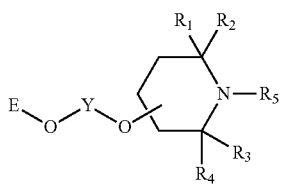
(I)

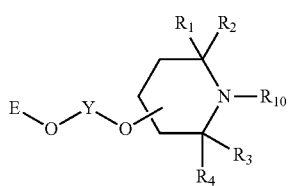
(Ib)

or a salt thereof or combinations thereof;
wherein:
$R_1$, $R_2$, $R_3$, $R_4$, and $R_5$ are each, independently, hydrogen or alkyl;
$R_{10}$ is —$OR_{11}$ wherein $R_{11}$ is hydrogen or alkyl, or —O.;
E represents a tocopheryl radical or a tocotrienol radical; and
Y represents the groups:

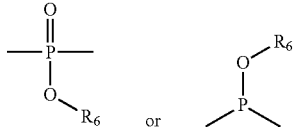

wherein $R_6$ is hydrogen, alkyl, a tocopheryl radical, a tocotrienol radical or a radical of the formula:

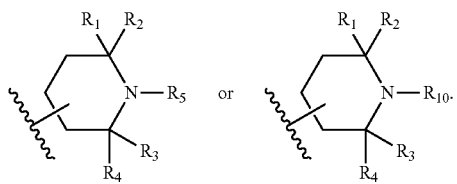

2. The composition of claim 1, wherein the at least one compound of the formula (I) are substantially uniformly distributed throughout the ultrahigh molecular weight polyethylene.

3. The composition of claim 1, wherein E or $R^6$ is a tocopheryl radical.

4. The composition of claim 1, wherein $R_6$ is a radical of the formula:

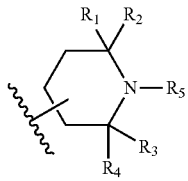

or a radical of the formula

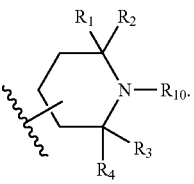

5. The composition of claim 1, wherein $R_1$, $R_2$, $R_3$, and $R_4$ are each, independently, alkyl.

6. The composition claim 1, wherein $R_5$ is alkyl.

7. The composition of claim 1, wherein Y represents the group:

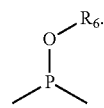

8. The composition of claim 1, wherein the at least one compound of formula (I) has the formula (Ia) or (Ic):

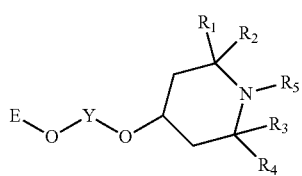
(Ia)

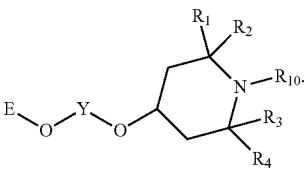
(Ic)

9. The composition of claim 1, wherein the ultrahigh molecular weight polyethylene is crosslinked.

10. The composition of claim 1, further comprising a cross-linking agent.

11. The composition of claim 10, wherein the cross-linking agent is a peroxide.

12. The composition of claim 10, wherein the cross-linking agent is a peroxide having a half-life ($t_{1/2}$) of about 1 hour at a temperature from about 180° C. to about 220° C.

13. An orthopedic implant comprising the composition of claim 1.

14. A method comprising:
combining an ultrahigh molecular weight polyethylene and the at least one compound of the formula (I) or (Ib):

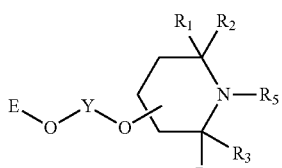

(I)

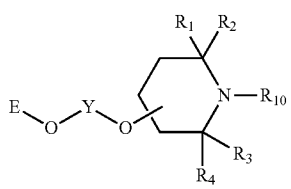

(Ib)

or a salt thereof or combinations thereof;
wherein:
R₁, R₂, R₃, R₄, and R₅ are each, independently, hydrogen or alkyl;
R₁₀ is —OR₁₁ wherein R₁₁ is hydrogen or alkyl, or —O.;
E represents a tocopheryl radical or a tocotrienol radical; and
Y represents the groups:

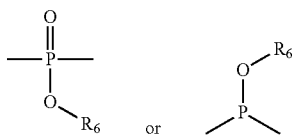

wherein R₆ is hydrogen, alkyl, a tocopheryl radical a tocotrienol radical or a radical of the formula:

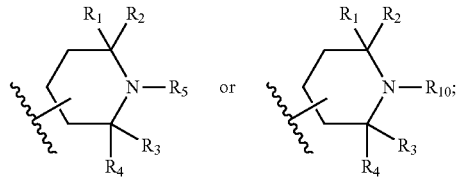

and
irradiating the combined ultrahigh molecular weight polyethylene and the at least one compound of the formula (I) to crosslink the ultrahigh molecular weight polyethylene.

15. The method of claim 14, further comprising converting at least some of the compound of the formula (I) to a compound of the formula EOH, wherein E represents a tocopheryl radical or a tocotrienol radical, after the irradiating step.

16. The method of claim 14, further comprising combining the ultrahigh molecular weight polyethylene and the at least one compound of formula (I) to provide a composition wherein the at least one compound of formula (I) is substantially uniformly distributed throughout the ultrahigh molecular weight polyethylene.

17. The method of claim 14, wherein the irradiating comprises irradiating with gamma radiation or electron beam radiation.

18. The method of claim 14, further comprising solidifying the combined ultrahigh molecular weight polyethylene and the at least one compound of the formula (I) prior to the irradiating step.

19. The method of claim 14, further comprising solidifying the combined ultrahigh molecular weight polyethylene and the at least one compound of the formula (I) after the irradiating step.

20. A method comprising:
combining an ultrahigh molecular weight polyethylene, the at least one compound of the formula (I) or (Ib):

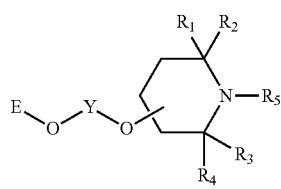

(I)

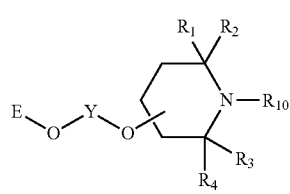

(Ib)

or a salt thereof or combinations thereof;
wherein:
R₁, R₂, R₃, R₄, and R₅ are each, independently, hydrogen or alkyl;
R₁₀ is —OR₁₁ wherein R₁₁ is hydrogen or alkyl, or —O.;
E represents a tocopheryl radical or a tocotrienol radical; and
Y represents the groups:

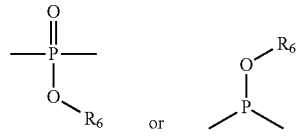

wherein R₆ is hydrogen, alkyl, a tocopheryl radical a tocotrienol radical or a radical of the formula:

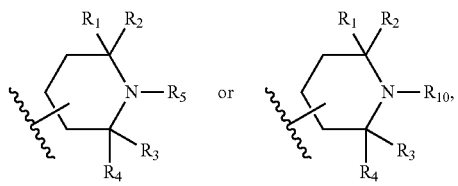

and
a cross-linking agent;
heating the combined ultrahigh molecular weight polyethylene, the at least one compound of the formula (I), and cross-linking agent to a temperature where there is substantial consolidation of the ultrahigh molecular weight polyethylenene, but there is not a substantial amount of cross-linking of the ultrahigh molecular weight polyethylene.

* * * * *

UNITED STATES PATENT AND TRADEMARK OFFICE
CERTIFICATE OF CORRECTION

PATENT NO. : 9,708,467 B2
APPLICATION NO. : 15/026153
DATED : July 18, 2017
INVENTOR(S) : Dirk Pletcher It is certified that error appears in the above-identified patent and that said Letters Patent is hereby corrected as shown below:

On the Title Page

On page 6, in Column 2, under "Other Publications", Line 32, delete "Morecular" and insert --Molecular-- therefor On page 6, in Column 2, under "Other Publications", Line 36, delete "molecularweight" and insert --molecular weight-- therefor On page 6, in Column 2, under "Other Publications", Line 37, delete "a-tocopherol" and insert --α-tocopherol-- therefor On page 6, in Column 2, under "Other Publications", Line 40, delete "a-tocopherol in y-irradiated" and insert --α-tocopherol in γ-irradiated-- therefor On page 6, in Column 2, under "Other Publications", Line 43-44, delete "a-tocopherol upon y-irradiation" and insert --α-tocopherol upon γ-irradiation-- therefor On page 6, in Column 2, under "Other Publications", Line 52, delete "photoxidation" and insert --photooxidation-- therefor On page 7, in Column 1, under "Other Publications", Line 24, delete ""Alpha-Tocopherol-doped" and insert --"α-Tocopherol-doped-- therefor On page 7, in Column 1, under "Other Publications", Line 27, delete "a-Tocopherol" and insert --α-Tocopherol-- therefor On page 7, in Column 1, under "Other Publications", Line 31-32, delete "alpha-tocopherol" and insert --α-tocopherol-- therefor Signed and Sealed this
Tenth Day of April, 2018

Andrei Iancu
*Director of the United States Patent and Trademark Office*

CERTIFICATE OF CORRECTION (continued)
U.S. Pat. No. 9,708,467 B2

On page 7, in Column 2, under "Other Publications", Line 9, delete "a-tocopherol" and insert --α-tocopherol-- therefor On page 7, in Column 2, under "Other Publications", Line 20, delete "alpha-tocopherol" and insert --α-tocopherol-- therefor In the Claims In Column 29, Line 64, in Claim 3, delete "$R^6$" and insert --$R_6$-- therefor